United States Patent [19]

Eriksoo et al.

[11] Patent Number: 4,738,971
[45] Date of Patent: * Apr. 19, 1988

[54] N-ARYL-1,2-DIHYDRO-4-SUBSTITUTED-1-ALKYL-2-OXO-QUINOLINE-3-CARBOXAMIDES

[75] Inventors: Edgar Eriksoo, Helsingborg; Eva B. M. Sandberg, Löddeköpinge; Lars J. T. Stalhandske, Helsingborg, all of Sweden

[73] Assignee: Aktiebolaset Leo, Helsingborg, Sweden

[*] Notice: The portion of the term of this patent subsequent to Oct. 15, 2002 has been disclaimed.

[21] Appl. No.: 723,746

[22] Filed: Apr. 16, 1985

Related U.S. Application Data

[63] Continuation of Ser. No. 350,890, Feb. 22, 1982, Pat. No. 4,547,511.

[30] Foreign Application Priority Data

Mar. 3, 1981 [GB] United Kingdom ................ 8106594

[51] Int. Cl.$^4$ .................... C07D 215/22; A61K 31/47
[52] U.S. Cl. .................................... 514/312; 514/291; 546/90; 546/156; 546/157; 546/158
[58] Field of Search .............. 546/155, 156, 157, 158; 514/312, 291

[56] References Cited

U.S. PATENT DOCUMENTS 3,960,868  6/1976  Ferrini et al. ...................... 546/155
4,547,511 10/1985  Erikson ............................. 546/158

FOREIGN PATENT DOCUMENTS 2705446  8/1977  Fed. Rep. of Germany ...... 546/156
 578534  8/1976  Switzerland .
 578537  8/1976  Switzerland .
1121411  7/1968  United Kingdom ................ 546/155

OTHER PUBLICATIONS

Coppola et al., "Chemistry of 2H-3,1-Benzoxazine-2,4(1H)dione . . . to form Quinolines," *J. Heterocyclic Chem*-16,1605 (1979).
Shridhar et al., ". . . Activity of 3,4-Disubstituted 2-oxo-1,2-dihydroquinolines, " *Indian J. Chem* 17B(1978), 488-490.
Chemical Abstract for Swiss Patent #578537 (8/13/76), 86:29657f (1977), Ferrini et al. II.
Chemical Abstract for Japan Patent #23,948 (10/16/68), 70:57681x (1969), Okumura et al.
Rocklin, R. E., Ann. Repts. Med. Chem., 8 (1973), 284.
Eisen, H. N., Immunology, Harper & Row Publishers, Inc., pp. 558-570 (1974).
Huskisson, E. C. et al., Lancet, 1 (1976), 393.
Dieppe, P. A. et al., Agents and Actions, 6/5 (1976), 618.
Winter, C. A. et al., Proc. Soc. Exp. Biol. Med. 111 (1962), 544.
Jones, G. (Ed.), Quinolines, part 1, John Wiley and Sons (1977), pp. 93-318.
Coppola, G. M. et al., J. Org. Chem., 41 (1976), 825.
Coffey, S. (Ed.), Rodd's Chemistry of Carbon Compounds, Elsevier Scientific Publishing Company, Amsterdam, 2nd Ed., vol. III, part B (1974), pp. 219-244.
Dieckmann, W. et al., Ber. 37 (1904), 4627.
Hardtmann; G. E. et al., J. Heterocycl. Chem., 12 (1975), 563.
Rügheimer, L. et al., Ber 17 (1884), 736.
Newbould, B. B., Brit. J. Pharmacol., 21 (1963), 127.
Shridhar, D. R. et al., Indian Journal of Chemistry, vol. 17B (1979), pp. 488-490.
Burger, A. et al., Progress in Drug Research, 20 (1976), pp. 347-383.
Flower; R. J. et al., Goodman and Gilman, 6 (1980), pp. 682, 686.
Renoux, G., Pharmac. Ther. A 2 (1978) 397.

*Primary Examiner*—Donald G. Daus
*Assistant Examiner*—E. Bernhardt
*Attorney, Agent, or Firm*—Fred Philpitt

[57] ABSTRACT

This invention relates to novel heterocyclic carboxamides which increase the activity of the immune system and to the preparation thereof. The invention is also concerned with pharmaceutical compositions containing the said compounds and methods of treatment therewith.

11 Claims, No Drawings

N-ARYL-1,2-DIHYDRO-4-SUBSTITUTED-1-ALKYL-2-OXO-QUINOLINE-3-CARBOXAMIDES

This is a continuation of application Ser. No. 350,890, filed Feb. 22, 1982, now U.S. Pat. No. 4,547,511, issued Oct. 15, 1985.

BACKGROUND OF THE INVENTION

1. Field of Invention

Certain heterocyclic carboxamides, certain dihydro-1,4-disubstituted-quinoline-3-carboxylic acid amides; increasing the activity of the immune system; compounds per se, compositions thereof, methods of treating therewith.

2. Prior Art

The immune system of the body has long been the subject of concerted study. A vigorous search has been made for drugs which influence the immune system. Numerous drugs which suppress the activity of the immune system have been found and, more recently, some compounds have been discovered which increase the activity of the immune system of the body. Some of these rather recently-discovered compounds have been found capable of increasing the activity of the cell-mediated immunity of the host. The study of such compounds for such purpose is a branch of science which is still in its infancy, but of obviously great significance in view of the possibility of increasing immunity of a host by the administration of a drug. The far-reaching effect of such research is apparent to all skilled in the art.

To the best of our knowledge, no compounds even remotely related structurally to the active compounds of the present invention have been suggested as activators of cell-mediated immunity. The closest prior art known to us is represented by an article in the Indian Journal of Chemistry Vol. 17 B, May 1979, pp. 488–490 (reported in Chemical Abstracts 93 (1980), page 667, entry 2044220.) This article discloses compounds which are structurally related to the compounds claimed in the present application. These previously known compounds exhibit anti-inflammatory activity as evidenced by a decrease in extent of carrageenan-induced edema in the carrageenan edema test.

The compounds according to the present invention, used for fundamentally different pharmacological purposes, do in fact, completely unexpectedly, increase the extent of carrageenan-induced edema in the test mentioned above (cf below and Table I of the present application), i.e. the compounds according to the present invention exhibit effects contrary to the effects exhibited by the previously known compounds.

Another type of compounds are disclosed in the Swiss Pat. Nos. 578,534, 578,535, 578,536, and 578,537, which relate to compounds suggested for different pharmacological uses, e.g. as antiinflammatory agents like the compounds disclosed in the Indian Journal of Chemistry. These compounds differ from the active compounds of the present invention structurally in that they all possess a cycloaliphatic radical as substituent on the benzene ring of the quinoline nucleus, and in that they fail to show or suggest the essential substituents in the amide portion of the molecule. More remote structurally related compounds, namely 2,4-dihydroxyquinoline-3-carboxylic amides, have been reported in Japanese Pat. No. 6,823,948 (Cl. 16 E 432) of approximately Oct. 16, 1968, reported in Chemical Abstracts 70 (1969) on page 355, entry 57681x. The compounds there reported are said to be useful as bactericides, and no possible use in the activation of any immune system is suggested for those compounds.

Another type of quinoline-3-carboxylic amide wherein the amide portion of the molecule contains certain heterocyclic rings and which may also include 2,4-dihydroxy-substituted compounds, has been reported in the Swedish patent application No. 7700804-3, reported in Chemical Abstracts 87 (1977) on page 578, entry 152042z. The reported compounds are said to be useful as analgetics, and no possible use in the activation of any immune system is suggested for these compounds.

FURTHER BACKGROUND OF THE INVENTION

In the following, references to the literature are given by numbers within brackets. The numbers refer to literature sources listed after the examples.

Cell-mediated immunity is considered a major defence system against many infectious agents and neoplasms (1, 2). Diseases such as rheumatoid arthritis and autoimmune disorders such as systemic lupus erythematosus are also attributed to impaired cell-mediated immunity. Agents which can stimulate impaired cell-mediated immunity are consequently of great potential value in the treatment of the above-mentioned diseases. An important expression of cell-mediated immunity is the delayed hypersensitivity reaction (1). An increase of this reaction therefore indicates enhanced cell-mediated immunity in the host (3).

A useful test for the evaluation of the effect of chemical compounds on the immune system is the pertussis vaccine pleurisy test in rats. Compounds which enhance the response in this delayed hypersensitivity reaction are considered to stimulate cell-mediated immunity (4).

The adjuvant arthritis test in rats produces a measureable extent of a delayed hypersensitivity reaction and can be used for a determination of variations in the extent of the delayed hypersensitivity reaction upon drug administration to the host. An increase in the extent of the delayed hypersensitivity reaction upon drug administration consequently indicates enhanced cell-mediated immunity in the host.

Another test, in which the effect of a drug corresponds to the effects obtained in the tests mentioned above, and which can therefore also be used, is the well-established carrageenan edema test in rats (5). Comparative evaluation of compounds of the present invention in the three tests mentioned has shown that compounds which increase the extent of the delayed hypersensitivity reaction in the pertussis vaccine pleurisy test and in the adjuvant arthritis test also increase the extent of carrageenan-induced edema in the carrageenan edema test, thus providing a further tool for the determination of enhancement of cell-mediated immunity.

We have now prepared a group of new heterocyclic carboxamides and have found that they are highly active in the tests which demonstrate an enhancing effect upon cell-mediated immunity. These compounds have also been found to have a low toxicity, resulting in a favourable therapeutic index. The potential significance of the present invention will, accordingly, be immediately apparent to one skilled in the art to which the invention pertains.

GENERAL DESCRIPTION OF THE INVENTION

The new heterocyclic carboxamides of the present invention correspond to the general formula I as defined below.

The compounds of the invention have shown a potentiating effect in the carrageenan edema test in rat, in adjuvant arthritis in respect of the secondary symptoms, and in the pertussis vaccine pleurisy test.

The compounds of the invention can be employed in disorders responsive to treatment with agents which enhance cell-mediated immunity as such or combined with either solid or liquid carriers or diluents and made available in varying amounts in such pharmaceutical form as eg tablets, pills, capsules, pellets, powders, ointments, suppositories, aqueous or non-aqueous suspensions and solutions.

OBJECT OF THE INVENTION

Accordingly, one object of the invention is to provide new compounds having the general formula I, having the aforesaid activity, preferably also with a low degree of toxicity.

A second object is to provide such type of compounds which can be employed in disorders, which are responsive to treatment with agents which enhance cell-mediated immunity, for the amelioration or palliation thereof.

Another object of the invention is to provide processes for preparing the new compounds having the general formula I.

A further object of the invention is to provide a method of treating a living animal body suffering from a disorder which is responsive to treatment with agents which enhance cell-mediated immunity, for the amelioration or palliation thereof, which comprises the step of administering to said living animal body a compound having the general formula I, said compound being administered in an amount sufficient to at least mitigate said disorder.

Yet another object of the invention is to provide compositions containing as an active ingredient one or more of the compounds having the general formula I, preferably together with a pharmaceutically acceptable carrier and, if desired, other pharmacologically active agents.

Other objects of the invention will become apparent to one skilled in the art, and still other objects will become apparent hereinafter.

SUMMARY OF THE INVENTION

Accordingly, what we believe and claim to be our invention comprises compounds having the general formula:

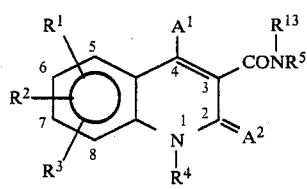

and the tautomers thereof, wherein the groups $A^1$ and $A^2$ are interchanged and there is a 2,3- rather than a 3,4-double bond; where $R^1$, $R^2$ and $R^3$ are the same or different and selected from the group consisting of: hydrogen; lower alkyl; lower alkoxy; halogen; $NO_2$; OH; $OCOR^8$; $NR^6R^7$; and $NR^6COR^8$; and where $R^1$ and $R^2$ or $R^2$ and $R^3$ together may also be in the form of a methylenedioxy group; where $R^4$ is selected from the group consisting of: lower alkyl; lower alkenyl; lower alkylene forming a ring with the 8-position carbon atom of the quinoline ring system; cycloalkyl, optionally mono- or disubstituted with substituents selected from the group consisting of lower alkyl, lower alkoxy, OH, and $OCOR^8$; and phenyl, optionally mono- or disubstituted with substituents selected from the group consisting of lower alkyl, lower alkoxy and halogen, especially F, Cl, and Br; and where $R^5$ is selected from the group consisting of: a five- or six-membered heterocyclic ring containing at most two heteroatoms selected from the groups consisting of S, and N, and being optionally mono- or disubstituted; with substituents selected from the group consisting of lower alkyl, lower alkoxy, and halogen, especially F and Cl; and the group:

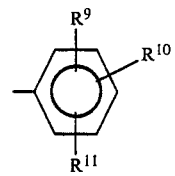

wherein $R^9$, $R^{10}$, and $R^{11}$ are the same or different and selected from the group consisting of: hydrogen; lower alkyl; lower alkenyl; lower alkoxy; lower alkylthio; halogen; CN; $SO_2CH_3$; OH; $OCOR^8$; $NR^6R^7$; $NR^6COR^8$; $COOR^{12}$; $OCH_2COOR^{12}$; $CH_2COOR^{12}$; $COR^8$; and

wherein m is four or five; and where $R^9$ and $R^{10}$ or $R^{10}$ and $R^{11}$ together also may be in the form of a methylenedioxy group; wherein $A^1$ is selected from the group consisting of $OR^{12}$, $OCOR^8$, $NR^6R^7$ and $NR^6COR^8$ and $A^2$ is selected from the group consisting of O and $NR^6$; wherein $R^6$ and $R^7$ are selected from the group consisting of hydrogen and lower alkyl; wherein $R^8$ is lower alkyl; wherein $R^{12}$ is selected from the group consisting of lower alkyl and M; and wherein M is selected from the group consisting of hydrogen and pharmaceutically acceptable inorganic and organic cations; and wherein $R^{13}$ is selected from the group consisting of hydrogen, lower alkyl, optionally substituted with a substituent selected from the group consisting of OH, $OR^8$ and $OCOR^8$, and lower alkenyl; provided that $R^{13}$ is selected fromn the group consisting of lower alkyl, optionally substituted with a substituent selected from the group consisting of OH, $OR^8$ and $OCOR^8$, and lower alkenyl when $R^9$, $R^{10}$ and $R^{11}$ are selected from the group consisting of lower alkyl, lower alkenyl and lower alkoxy.

The compounds of the present invention which contain salt-forming basic nitrogen atoms may also be in the form of addition salts with pharmaceutically acceptable inorganic or organic acids, the salts thus formed being such as the hydrochlorides, hydrobromides, phosphates, nitrates, sulphates, hydrogenoxalates, oxalates, succinates, tartrates, methanesulphonates, and ethanedisulphonates.

In this disclosure the expression "lower" means that the group referred to contains one to four carbon atoms, inclusive. Thus, lower alkyl, lower alkenyl, lower alkylene, lower alkoxy, and lower alkanols include for instance: methyl, ethyl, propyl, iso-propyl, butyl, scondary butyl, iso-butyl, tertiary butyl, vinyl, iso-propenyl, 1-propenyl, allyl, ethylene, trimethylene, propylene, tetramethylene, 1,2-dimethylethylene, ethylethylene, 1-methyltrimethylene, 2-methyltrimethylene, methoxy, ethoxy, propoxy, isopropoxy, butoxy, isobutoxy, secondary butoxy, tertiary butoxy, methanol, ethanol, propanol, isopropanol, butanol, iso-butanol, secondary butanol, and tertiary butanol.

Among pharmaceutically acceptable inorganic and organic cations under the definition of M above, those derived from the following metals and amines may be mentioned as representative: metals: calcium, potassium, and sodium; amines: monoethanolamine, diethanolamine, dimethylaminoethanol, N-methylglucamine, trihydroxymethylmethylamine, morpholine, and the like.

Among the compounds covered by the above general formula I or its tautomers, those are preferred wherein at least one of $R^1$, $R^2$, and $R^3$ is hydrogen.

With regard to the substituents $R^1$, $R^2$, and $R^3$, it is preferred that these substituents are hydrogen, lower alkyl, lower alkoxy, halogen, OH, $OCOR^8$, $NR^6R^7$, and methylenedioxy.

When $R^1$, $R^2$, and $R^3$ are halogen or $NR^6R^7$ it is preferred that only one of $R^1$, $R^2$, and $R^3$ consists of one of said substituents.

If selected from halogen atoms it is preferred that $R^1$, $R^2$, or $R^3$ is F, Cl, or Br, especially F and Cl.

Other groups of preferred compounds are those where $R^4$ is lower alkyl. When $R^4$ is a lower alkyl group a methyl group is preferred.

When $R^4$ is lower alkylene forming a ring with the 8-position carbon atom of the quinoline ring system such types of compounds have a stable configuration and are therefore of special interest, whereby ethylene and trimethylene groups are preferred as the lower alkylene groups.

When $R^4$ is substituted phenyl, monosubstitution in p-position is preferred.

When $R^4$ is cycloalkyl, cyclopentyl and cyclohexyl are preferred and, if the cycloalkyl ring is substituted, monosubstitution is preferred.

If $R^5$ is the group II above it is preferred that at least one of the substituents $R^9$, $R^{10}$, and $R^{11}$ is hydrogen and, when two of said substituents are hydrogen, it is also preferred that the remaining substituent is situated in the p-position.

If selected from lower alkylthio, halogen, CN, $SO_2CH_3$, OH, $OCOR^6$, $NR^6R^7$, $NR^6COR^8$, $COOR^{12}$, $OCH_2COOR^{12}$, $CH_2COOR^{12}$, $COR^8$, or

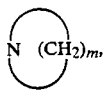

preferably only one of the substituents $R^9$, $R^{10}$, and $R^{11}$ is selected from said groups.

When one pair of the substituents $R^9$, $R^{10}$, and $R^{11}$ forms a methylenedioxy group, it is preferred that said group is situated in m- and p-positions.

When $R^5$ is a five- or six-membered heterocyclic ring, and the heterocyclic ring contains two heteroatoms of the same kind, N is preferred.

When $R^5$ is a heterocyclic ring, the following heterocyclic ring systems are of special interest in the present invention:

Pyridine, pyrazole, imidazole, iso-thiazole, thiazole, pyridazine, pyrimidine, and pyrazine, especially pyridine, imidazole, thiazole and pyrazine.

When $R^5$ is substituted heterocyclic ring monosubstitution is preferred.

When $A^1$ is $OR^{12}$ or $OCOR^8$ it is preferred that $A^2$ is O.

When $A^1$ is $NR^6R^7$ or $NR^6COR^8$ it is preferred that $A^2$ is O.

When $A^2$ is $NR^6$ it is preferred that $A^1$ is $OR^{12}$ or $OCOR^8$.

When $A^1$ is $OR^{12}$ it is preferred that $R^{12}$ is M.

When $R^{12}$ is a lower alkyl group, methyl and ethyl groups are preferred.

When M is an inorganic cation, potassium and sodium ions are preferred.

If one of $A^1$ or $A^2$ is $NR^6R^7$, $NR^6COR^8$ or $NR^6$ it is preferred that $R^5$ is the above group II.

Another group of preferred compounds which are of special interest in the present invention is the one where $R^{13}$ is lower alkyl, optionally substituted with a substituent selected from OH, $OR^8$ or $OCOR^8$, or lower alkenyl, especially lower alkyl.

When $R^{13}$ is lower alkyl, optionally substituted with a substituent selected from OH, $OR^8$ or $OCOR^8$, or lower alkenyl it is preferred that one of the substituents $R^9$, $R^{10}$, and $R^{11}$ is lower alkyl, lower alkoxy or halogen, especially F and Cl.

When $R^{13}$ is hydrogen it is preferred that one of the substituents $R^9$, $R^{10}$, and $R^{11}$ is halogen, OH, $OCOR^8$, $NR^6R^7$, $NR^6COR^8$, $COOR^{12}$, $OCH_2COOR^{12}$, $CH_2COOR^{12}$ or

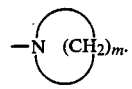

When $R^{13}$ is hydrogen it is also preferred that one of the substituents $R^9$, $R^{10}$ and $R^{11}$ is a group which confers water solubility to the compound hereby obtained.

When $R^{13}$ is lower alkyl, optionally substituted with a substituent selected from OH, $OR^8$ or $OCOR^8$, or lower alkenyl it is also preferred that $A^1$ is OH, $A^2$ is O, $R^4$ is lower alkyl and RHU 5 is the group II as defined above.

When $R^{13}$ is hydrogen it is also preferred that $R^4$ is lower alkyl and $R^5$ is a heterocyclic ring.

When $A^1$ is $NR^6R^7$ or $NR^6COR^8$ it is preferred that $A^2$ is O, $R^4$ is lower alkyl and $R^5$ is the group II as defined above. The following compounds are preferred:

(a) N-(4-dimethylaminophenyl)-1,2-dihydro-4-hydroxy-1-methyl-2-oxo-quinoline-3-carboxamide (b) N-(4-carboxymethylphenyl)-1,2-dihydro-4-hydroxy-1-methyl-2-oxo-quinoline-3-carboxamide (c) N-(4-hydroxyphenyl)-1,2-dihydro-4-hydroxy-1-methyl-2-oxo-quinoline-3-carboxamide (d) N-phenyl-N-methyl-1,2-dihydro-4-hydroxy-1-methyl-2-oxo-quinoline-3-carboxamide (e) N-phenyl-1,2-dihydro-1,8-ethylene-4-hydroxy-2-oxo-quinoline-3-carboxamide (f) N-phenyl-1,2-dihydro-4-hydroxy-2-oxo-1,8-trimethylene-quinoline-3-carboxamide (g) N-(2-thiazolyl)-1,2-dihydro-4-hydroxy-1-methyl-2-oxo-quinoline-3-carboxamide (h) N-methyl-N-phenyl-4-amino-1,2-dihydro-1-methyl-2-oxo-quinoline-3-carboxamide (i) N-methyl-N-(2-thiazolyl)-4-amino-1,2-dihydro-1-methyl-2-oxo-quinoline (j) N-phenyl-1,2-dihydro-4-hydroxy-2-imino-1-methyl-quinoline-3-carboxamide (k) N-methyl-N-phenyl-1,2-dihydro-4-hydroxy-2-oxo-1,8-trimethylene-quinoline-3-carboxamide (l) N-methyl-N-phenyl-1,2-dihydro-6-dimethylamino-4-hydroxy-1-methyl-2-oxo-quinoline-3-carboxamide (m) N-(2-imidazolyl)-N-methyl-1,2-dihydro-4-hydroxy-1-methyl-2-oxo-quinoline-3-carboxamide (n) N-(4-methoxyphenyl)-N-methyl-1,2-dihydro-4-hydroxy-1-methyl-2-oxo-quinoline-3-carboxamide (o) N-methyl-N-(2-pyridyl)-1,2-dihydro-4-hydroxy-1-methyl-2-oxo-quinoline-3-carboxamide (p) N-(4-chlorophenyl)-N-methyl-1,2-dihydro-4-hydroxy-1-methyl-2-oxo-quinoline-3-carboxamide (q) N-methyl-N-pyrazinyl-1,2-dihydro-1,8-ethylene-4-hydroxy-2-oxo-quinoline-3-carboxamide (r) N-methyl-N-(2-thiazolyl)-1,2-dihydro-4-hydroxy-1-methyl-2-oxo-quinoline-3-carboxamide (s) N-methyl-N-pyrazinyl-1,2-dihydro-4-hydroxy-1-methyl-2-oxo-quinoline-3-carboxamide (t) N-methyl-N-(2-thiazolyl)-1,2-dihydro-1,8-ethylene-4-hydroxy-2-oxo-quinoline-3-carboxamide and (u) N-(2-hydroxyphenyl)-N-methyl-1,2-dihydro-4-hydroxy-1-methyl-2-oxo-quinoline-3-carboxamide.

If desired the above compounds may also be in the form of salts with pharmaceutically acceptable inorganic or organic cations or addition salts with pharamaceutically acceptable inorganic or organic acids.

METHODS OF PREPARATION

The compounds having the general formula I may be prepared by conventional methods.

A general process (Method 1 below) for preparing compounds having the general formula is as follows,

Method 1

Compounds of the general formula I are prepared by reacting a carboxylic acid III or a reactive derivative thereof

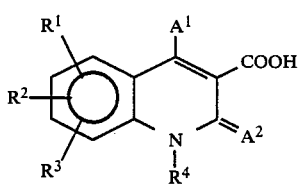

III with an amine $R^5R^{13}NH$ or a reactive derivative thereof.

Among other methods for preparing compounds having the general formula I the following may be mentioned,

Method 2

A reactive derivative of a dicarboxylic acid IV.

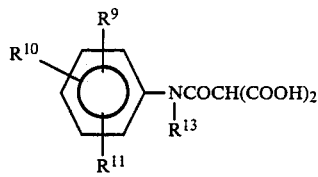

IV is reacted with an amine

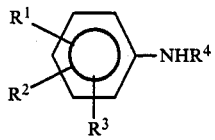

V to form compounds of the general formula I, wherein $A^1$ is OH and $A^2$ is O.

Method 3

A derivative of isatoic anhydride of the general formula VI

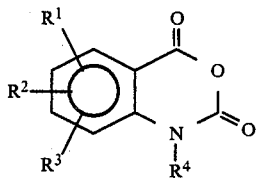

VI is reacted with a lower alkyl ester of an acid VII $$R^5R^{13}NCOCH_2COOH \qquad \text{VII}$$

to form compounds of the general formula I, wherein $A^1$ is OH and $A^2$ is O, or reacted with a nitrile VIII $$R^5R^{13}NCOCH_2CN \qquad \text{VIII}$$

to form compounds of the general formula I, wherein $A^1$ is OH and $A^2$ is NH.

Method 4

A compound of the general formula IX

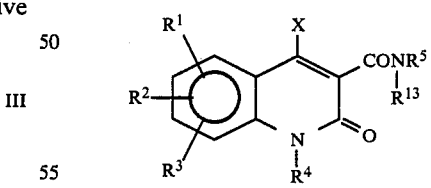

IX wherein X is halogen, preferably Cl or Br, is reacted with a compound $A^1H$ or a reactive derivative thereof to form compounds of the general formula I, wherein $A^2$ is O.

Methods 1–4 above are illustrated by the following processes (a–d), (a) A process according to method 1, characterized by reacting a carboxylic acid III or a reactive derivative thereof with an amine $R^5R^{13}NH$. or a reactive derivative thereof.

Having a reactive derivatve of III the reaction may be carried out by mixing the reagents in an inert solvent medium at a temperature between 0° and 200° C. depending on the reactivity of the reactive derivative of the carboxylic acid III used. As such reactive derivatives the following conventional types may be mentioned: lower alkyl esters (preferably methyl or ethyl esters), anhydrides, acid chlorides, mixed anhydrides with aliphatic or aromatic sulphonic acids, and reactive derivatives obtained with carbodiimides and similar reagents.

Pyridine and quinoline are especially suitable as inert solvents.

The carboxylic acids III and reactive derivatives thereof may be prepared by conventional methods as described in (6).

More specifically the lower alkyl esters of the carboxylic acid III may be prepared by the method described in (7).

The amines $R^5R^{13}NH$ are known compounds or can be prepared by conventional methods as described in (8).

The process according to method I may also be carried out by reacting the carboxylic acid III with a reactive derivative of the amine $R^5R^{13}NH$.

Such reactive derivatives may be compounds formed by mixing the amine $R^5R^{13}NH$ with a phosphorous compound such as phosphorous trichloride. The reaction may be carried out by mixing the reagents in an inert solvent medium and heating at a temperature between 0° C. and the boiling point of the reaction mixture.

(b) A process according to method 2, characterized by reacting a reactive derivative of a dicarboxylic acid IV with an amine V. The reaction may be carried out by mixing the reagents in an inert solvent medium and heating at a temperature above 100° C., preferably between 150° and 250° C.

As reactive derivatives of the dicarboxylic acid IV methyl, ethyl, or phenyl esters may be used.

Diphenyl ether is a suitable solvent for the process.

The reactive derivatives of the dicarboxylic acid IV are known compounds or can be prepared according to the general method described in (9). The amines V are known compounds or may be prepared by conventional methods as described in (8).

(c) A process according to method 3, characterized by reacting an isatoic anhydride derivative VI with a lower alkyl ester of an acid VII in the presence of a proton acceptor. Methyl and ethyl esters are preferred.

As examples of proton acceptors which may be used in this reaction the following may be mentioned: alkali alkoxides such as sodium methoxide and sodium hydride.

The reaction is preferably carried out in an inert solvent such as dimethylformamide, or in a solvent which is also a portion acceptor such as pyridine or quinoline.

The reaction is preferably carried out above room temperature, preferably between 50° and 150° C.

The starting materials VI are known compounds or may be prepared by methods described in (10).

The lower alkyl esters of the acid VII are known compounds or may be prepared by using the general method described in (11).

When the nitrile VIII is used in this process a compound I wherein $A^1$ is OH and $A^2$ is NH is obtained. The nitriles VIII are known compounds or may be prepared by using known methods.

(d) A process according to method 4 characterized by converting the halogen substituent X in compound IX to a group $A^1$ may be carried out by using conventional methods. One such method is a reaction of IX with aqueous solutions of hydroxides of sodium or potassium between room temperature and the boiling point of the reaction mixture. Another method is reacting the compound IX with an alkali salt of an alkanoic acid, preferably in an aprotic dipolar solvent such as dimethylformamide, dimethylacetamide, or dimethyl sulphoxide followed by hydrolysis. Both these methods give compounds I wherein $A^1$ is OH.

If a compound I wherein $A^1$ is $OR^{12}$, wherein $R^{12}$ is lower alkyl is desired, this may be produced by reacting a compound IX with a compound containing a reactive alkoxide ion such as an alkali lower alkoxide. The reaction is preferably carried out in an inert solvent medium between room temperature and the boiling point of the reaction mixture.

If a compound I wherein $A^1$ is $NR^6R^7$ is desired, this may be produced by reacting a compound IX with an amine $NR^6R^7H$. The reaction is preferably carried out in an inert solvent medium between room temperature and 200° C. The reaction may if necessary be carried out under pressure.

The starting materials of the formula IX may be prepared by the general method illustrated in Example 4 below.

All the above processes, a–d, may optionally be carried out in the presence of a catalyst known to be useful in said processes.

It is also possible in a manner known per se to prepare compounds having the general formula I above from other compounds within the definition of said general formula.

As examples of such transformations the following may be mentioned: Free hydroxy groups are, e.g., obtained by removal of acyl groups from carboxylic esters or by removal of lower alkyl groups from lower alkoxy groups. Free amino groups are, e.g., obtained by removal of acyl groups from carboxamides or by reduction of nitro groups. Free carboxylic acid groups are, e.g., obtained by hydrolysis of ester-, amide-, and nitrile groups. On the other hand, free hydroxy groups can be esterified and etherified, primary and secondary amines acylated to amides, and carboxylic acids esterified.

In synthesizing compounds having the general formula I by any of the methods mentioned above, each group of the starting materials involved must be compatible with the process in question or, if necessary, protected during one or more reaction steps and then converted to the desired group. Pertinent examples of groups that may be protected are hydroxy-, carboxyl-, and primary and secondary amino groups. Examples of such protecting groups are found in (14).

The compounds of the invention are generally characterized by the pharmacological activity hereinbefore stated, making them useful in counteracting certain physiological abnormalities in a living animal body. Effective quantities of the pharmacologically active compounds of the invention may be administered to a living animal body in any one of various ways, for example orally as in capsules or tablets, parenterally in the form of sterile solutions, suspensions, and by pellet implantation. Among routes of parenteral administration are intravenously, subcutaneously, intramuscularly, intraperitoneally, intraarticularly, and intradermally. Other modes of administration are vaginally, reactably, and topically as, e.g., in the form of ointments, suppositories, and powders.

As representative of living animal bodies, which may be treated with the compounds and compositions of the invention, and according to the method of treatment of the invention, for alleviation of the same and/or similar conditions as those described, in addition to homo sapiens the following may be mentioned: domestic animals such as dogs and cats and farm animals such as horses, cows, sheep, and goats.

Pharmaceutical formulations are usually prepared from a predetermined quantity of one or more of the compounds of the invention. Such formulations may take the form of powder, syrups, suppositories, ointments, solutions, pills, capsules, pellets or tablets, suspensions, emulsions, oil solutions, etc, with or without, but preferably with, any one of a large variety of pharmaceutically acceptable vehicles or carriers. When in a mixture with a pharmaceutical vehicle or carrier, the active ingredient usually comprises from about 0.01 to about 75 percent, normally from about 0.05 to about 15 percent, by weight of the composition. Carriers such as starch, sugar, talc, commonly used synthetic and natural gums, water, and the like, may be used in such formulations. Binders such as polyvinylpyrrolidone and lubricants such as sodium stearate, may be used to form tablets. Disintegrating agents such as sodium carbonate may also be included in tablets.

Although relatively small quantities of the active materials of the invention, even as low as 5.0 milligrams, may be used in cases of administration to subjects having a relatively low body weight, unit dosages are preferably five milligrams or above and preferably twenty-five, fifty, or one hundred milligrams, or even higher, depending of course upon the subject treated and the particular result desired, as will be apparent to one skilled in the art. Broader ranges appear to be 1 to 1000 milligrams per unit dose.

The active agents of the invention may be combined for administration with other pharmaceutically active agents such as analgesics, steroids or hormones, or the like, or with buffers, antacids, or the like, and the proportion of the active agent or agents in the compositions may be varied widely. It is only necessary that the active ingredient of the invention constitutes an effective amount, i.e., such that a suitable effective dosage will be obtained consistent with the dosage form employed. Obviously, several units dosage forms may be administered at about the same time. The exact individual dosage as well as daily dosages in a particular case will of course be determined according to well established medical and/or veterinary principles under the supervision of the physician or veterinarian in charge. As a rule, however, when used therapeutically, the present compounds may be administered in a quantity of 1 to 1000 milligrams, preferred ranges being 5–250 milligrams per day and subject or patient, divided in 1 to 4 or more doses, over a suitable period and depending upon the subject and the type of subject being treated.

DETAILED DESCRIPTION OF THE INVENTION

The following examples are intended to illustrate but not to limit the scope of the invention, although the compounds named are of particular interest for our intended purposes. These compounds have been designated by underlined numbers in the examples where their preparations are described and where their systematic names are given. The compounds are later on referred to by a number code, a:b, where a means the number of the example wherein the preparation of the compound in question is described, and b refers to the order of the compounds prepared according to that example. Thus, compound 1:2 means the second compound prepared according to Example 1.

The structures of the compounds found in Examples 1–21 are confirmed by NMR and elementary analysis. The NMR data are obtained using a 60 MHz instrument (Perkin-Elmer R 12). Most of the compounds prepared in the examples below have been isolated in free form. Some of them have been transformed into the salts with pharmaceutically acceptable cations or into acid addition salts by using conventional methods and appropriate reagents.

EXAMPLE 1

A mixture of 1,2-dihydro-4-hydroxy-1-methyl-2-oxo-quinoline-3-carboxylic acid ethyl ester (10 parts), aniline (4 parts), and pyridine (40 parts) is heated at 125° C. for 3 h. The ethanol formed is distilled off continuously. The product, N-phenyl-1,2-dihydro-4-hydroxy-1-methyl-2-oxo-quinoline-3-carboxamide (1), precipitates on cooling to room temperature and is filtered off and recrystallized from pyridine. M.p. 199°–200° C.

In essentially the same manner the following compounds are obtained from the corresponding starting materials.

2. N-phenyl-1,2-dihydro-4-hydroxy-6-methoxy-1-methyl-2-oxo-quinoline-3-carboxamide, m.p. 192°–3° C.
3. N-1-diphenyl-1,2-dihydro-4-hydroxy-2-oxo-quinoline-3-carboxamide, m.p. 260° C.
4. N-(3-hydroxyphenyl)-1,2-dihydro-4-hydroxy-1-methyl-2-oxo-quinoline-3-carboxamide
5. N-phenyl-1,2-dihydro-6-dimethylamino-4-hydroxy-1-methyl-2-oxo-quinoline-3-carboxamide, m.p. 193° C.
6. N-phenyl-1,2-dihydro-4,6-dihydroxy-1-methyl-2-oxo-quinoline-3-carboxamide, m.p. 252° C.
7. N-(4-carboxymethylphenyl)-1,2-dihydro-6,7-dimethoxy-4-hydroxy-1-methyl-2-oxo-quinoline-3-carboxamide
8. N-/2-chlorophenyl/-1,2-dihydro-4-hydroxy-1-methyl-2-oxo-quinoline-3-carboxamide, m.p. 211°–3° C.
9. N-/4-chlorophenyl/-1,2-dihydro-4-hydroxy-1-methyl-2-oxo-quinoline-3-carboxamide, m.p. 212°–3° C.
10. N-phenyl-1,2-dihydro-1-ethyl-4-hydroxy-2-oxo-quinoline-3-carboxamide m.p. 169°–72° C.
11. N-/4-dimethylaminophenyl/-1,2-dihydro-4-hydroxy-1-methyl-2-oxo-quinoline-3-carboxamide, m.p. 190°–2° C.
12. N-/4-carboxymethylphenyl/-1,2-dihydro-4-hydroxy-1-methyl-2-oxo-quinoline-3-carboxamide, m.p. 237°–9° C.
13. N-/4-hydroxyphenyl/-1,2-dihydro-4-hydroxy-1-methyl-2-oxo-quinoline-3-carboxamide, m.p. 233°–4° C.
14. N-phenyl-1,2-dihydro-4-hydroxy-1-isopropyl-2-oxo-quinoline-3-carboxamide, m.p. 155° C.
15. N-phenyl-1,2-dihydro-4-hydroxy-1-isobutyl-2-oxo-quinoline-3-carboxamide, m.p. 143° C.
16. N-phenyl-1,2-dihydro-4-hydroxy-2-oxo-1-n-propyl-quinoline-3-carboxamide, m.p. 149° C.
17. N-phenyl-7-chloro-1,2-dihydro-4-hydroxy-1-methyl-2-oxo-quinoline-3-carboxamide, m.p. 208° C.
18. N-phenyl-6-chloro-1,2-dihydro-4-hydroxy-1-methyl-2-oxo-quinoline-3-carboxamide, m.p. 200° C.

19. N-phenyl-1,2-dihydro-5-fluoro-4-hydroxy-1-methyl-2-oxo-quinoline-3-carboxamide, m.p. 175° C.
20. N-/4-nitrophenyl/-1,2-dihydro-4-hydroxy-1-methyl-2-oxo-quinoline-3-carboxamide, m.p. 300° C.
21. N-/4-methylaminophenyl/-1,2-dihydro-4-hydroxy-1-methyl-2-oxo-quinoline-3-carboxamide, m.p. 204° C.
22. N-phenyl-1,2-dihydro-4-hydroxy-8-methoxy-1-methyl-2-oxo-quinoline-3-carboxamide, m.p. 163° C.
23. N-/4-diethylaminophenyl/-1,2-dihydro-4-hydroxy-1-methyl-2-oxo-quinoline-3-carboxamide, m.p. 140° C.
24. N-/4-pyrrolidinophenyl/-1,2-dihydro-4-hydroxy-1-methyl-2-oxo-quinoline-3-carboxamide, m.p. 253° C.
25. N-(4-carboxymethoxyphenyl)-6-n-butyl-1,2-dihydro-4-hydroxy-1-methyl-2-oxo-quinoline-3-carboxamide
26. N-(4-methoxycarbonylmethoxyphenyl)-1,2-dihydro-4-hydroxy-1-methyl-2-oxo-quinoline-3-carboxamide
27. N-(3-n-butylthiophenyl)-6-n-butoxy-1,2-dihydro-4-hydroxy-1-methyl-2-oxo-quinoline-3-carboxamide.
28. N-(4-bromophenyl)-1,2-dihydro-4-hydroxy-1-methyl-2-oxo-quinoline-3-carboxamide.
29. N-(3-cyanophenyl)-6-bromo-1,2-dihydro-1-ethyl-4-hydroxy-2-oxo-quinoline-3-carboxamide.
30. N-(4-methylsulphonylphenyl)-1,2-dihydro-1-ethyl-4-hydroxy-2-oxo-quinoline-3-carboxamide.
31. N-/4-(N-n-butyl-N-n-propyl-amino)phenyl/-6-acetoxy-1,2-dihydro-1-ethyl-4-hydroxy-2-oxo-quinoline-3-carboxamide.
32. N-(4-methoxycarbonylmethyl-phenyl)-1,2-dihydro-6-dimethyl-amino-1-ethyl-4-hydroxy-2-oxo-quinoline-3-carboxamide
33. N-(4-carboxyphenyl)-6-n-butylamino-1,2-dihydro-4-hydroxy-1-methyl-2-oxo-quinoline-3-carboxamide, sodium salt.
34. N-(3-i-butyrylphenyl)-6-acetylamino-1,2-dihydro-4-hydroxy-1-methyl-2-oxo-quinoline-3-carboxamide.
35. N-(3,4-methylenedioxyphenyl)-1,2-dihydro-4-hydroxy-1-methyl-2-oxo-quinoline-3-carboxamide, m.p. 227° C.
36. N-(4-piperidinophenyl)-1,2-dihydro-4-hydroxy-1-methyl-6,7-methylenedioxy-2-oxo-quinoline-3-carboxamide, hydrochloride.
37. N-(4-n-butylaminophenyl)-1,2-dihydro-4,6-dihydroxy-1-methyl-2-oxo-quinoline-3-carboxamide.
38. N-(4-ethoxycarbonylmethylphenyl)-1-cyclohexyl-1,2-dihydro-4-hydroxy-2-oxo-quinoline-3-carboxamide.
39. N-phenyl-1-(4-chlorophenyl)-1,2-dihydro-4-hydroxy-2-oxo-quinoline-3-carboxamide.
40. N-phenyl-1-(3,4-dimethoxyphenyl)-1,2-dihydro-4-hydroxy-2-oxo-quinoline-3-carboxamide.
41. N-(4-acetylaminophenyl)-1,2-dihydro-4-hydroxy-1-methyl-2-oxo-quinoline-3-carboxamide, m.p. 231°-4° C.
42. N-phenyl-1,2-dihydro-4-hydroxy-1-methyl-5-nitro-2-oxo-quinoline-3-carboxamide, m.p. 260° C.
43. N-phenyl-N-methyl-1,2-dihydro-4-hydroxy-1-methyl-2-oxo-quinoline-3-carboxamide, m.p. 200°-204° C.
44. N-(4-allylphenyl)-N-methyl-1,2-dihydro-4-hydroxy-1-methyl-2-oxo-quinoline-3-carboxamide
45. N-(4-ethylaminophenyl)-1,2-dihydro-4-hydroxy-1-methyl-2-oxo-quinoline-3-carboxamide
46. N-phenyl-1,2-dihydro-1,6-dimethyl-4-hydroxy-2-oxo-quinoline-3-carboxamide, m.p. 201° C.
47. N-(4-dimethylaminophenyl)-1-allyl-1,2-dihydro-4-hydroxy-2-oxo-quinoline-3-carboxamide, m.p. 170°-173° C.
48. N-(4-acetylphenyl)-1,2-dihydro-4-hydroxy-1-methyl-2-oxo-quinoline-3-carboxamide, m.p. 212° C.
49. N-(3-methylmercaptophenyl)-1,2-dihydro-4-hydroxy-1-methyl-2-oxo-quinoline-3-carboxamide, m.p. 153° C.
50. N-phenyl-1,2-dihydro-4-hydroxy-1-(4-methylphenyl)-2-oxo-quinoline-3-carboxamide.
51. N-phenyl-1-allyl-1,2-dihydro-4-hydroxy-2-oxo-quinoline-3-carboxamide, m.p. 168°-71° C.
52. N-phenyl-1,2-dihydro-4-hydroxy-1-(4-methylcyclohexyl)-2-oxo-quinoline-3-carboxamide.
53. N-phenyl-1,2-dihydro-4-hydroxy-1-(4-methoxycyclohexyl)-2-oxo-quinoline-3-carboxamide, and
54. N-(4-pivaloyloxyphenyl)-1,2-dihydro-4-hydroxy-1-methyl-2-oxo-quinoline-3-carboxamide

EXAMPLE 2

A mixture of N-phenylcarbamoyl-dimethylmalonate (14 parts) and 4-methoxy-N-methyl-aniline (7 parts) is heated at 200° C. for 3 h. The methanol formed is distilled off continuously. The reaction mixture is poured into warm acetic acid, and the product, N-phenyl-1,2-dihydro-4-hydroxy-6-methoxy-1-methyl-2-oxo-quinoline-3-carboxamide (1) (the same compound as 1:2), precipitates and is filtered off. M.p. 192°-3° C.

In essentially the same manner the following compounds are obtained from N-phenylcarbamoyl-dimethylmalonate and indoline and 1,2,3,4-tetrahydroquinoline, respectively:

2. N-phenyl-1,2-dihydro-1,8-ethylene-4-hydroxy-2-oxo-quinoline-3-carboxamide, m.p. 215°-7° C., and
3. N-phenyl-1,2-dihydro-4-hydroxy-2-oxo-1,8-trimethylene-quinoline-3-carboxamide. m.p. 177°-8° C.

EXAMPLE 3

To a mixture of 27 parts of N-phenylcarbamoyl acetic acid ethyl ester in 75 parts of dimethylformamide are added 5.3 parts of a 60% suspension of sodium hydride in mineral oil. The mixture is heated at 80° C. for 15 minutes. A solution of 22 parts of N-methyl isatoic anhydride (=1-methyl-2H-3,1-benzoxazine-2,4(1H)dione) in 125 parts of dimethylformamide is added. The reaction mixture is then heated at 110° C. for 30 minutes and cooled to room temperature. The crystalline precipitate is filtered off, and methylene chloride and aqueous hydrochloric acid are added. After shaking until clear phases are obtained, the methylene chloride phase is washed with water and evaporated to dryness in vacuo. The residue is crystallized from pyridine to give N-phenyl-1,2-dihydro-4-hydroxy-1-methyl-2-oxo-quinoline-3-carboxamide (1) (the same compound as 1:1). M.p. 199°-200° C.

EXAMPLE 4

A mixture of 46 parts of 1,2-dihydro-4-hydroxy-1-methyl-2-oxo-quinoline-3-carboxylic acid methyl ester and 240 parts of phosphorous oxychloride is heated at 80° C. for 2 h. The excess of phosphorous oxychloride is distilled off in vacuo. The residue is cooled to 0° C. and dissolved in methanol. Ice and water are added. The crystals of 1,2-dihydro-4-chloro-1-methyl-2-oxo-quinoline-3-carboxylic acid methyl ester precipitate are filtered off and dried. M.p. 108° C.

A mixture of 65 parts of 1,2-dihydro-4-chloro-1-methyl-2-oxo-quinoline-3-carboxylic acid methyl ester, 17.3 parts of 63% aqueous hydrobromic acid, and 36.3 parts of acetic anhydride is heated at 65° C. for 4 h and then left overnight at room temperature. The crystals formed are filtered off and then dissolved in aqueous sodium hydroxide solution and extracted with methylene chloride.

The aqueous phase is acidified. The crystals of 1,2-dihydro-4-chloro-1-methyl-2-oxo-quinoline-3-carboxylic acid precipitate are filtered off and dried. M.p. 228° C.

A mixture of 13.8 parts of 1,2-dihydro-4-chloro-1-methyl-2-oxo-quinoline-3-carboxylic acid, 60 parts of methylene chloride, and 12.4 parts of triethylamine is cooled to −10° C., and a solution of 7.3 parts of thionyl chloride in 18 parts of methylene chloride is added dropwise while stirring the reaction mixture. The stirring is continued at 0° C. for 1.5 h whereafter 6.3 parts of aniline are added dropwise at −10° C., and the temperature is then allowed to rise to room temperature. Ice-water is added, and the crystals of N-phenyl-1,2-dihydro-4-chloro-1-methyl-2-oxo-quinoline-3-carboxamide are filtered off and dried. M.p. >260° C.

A mixture containing one part of each of anhydrous sodium acetate, dimethylformamide, and N-phenyl-4-chloro-1,2-dihydro-1-methyl-2-oxo-quinoline-3-carboxamide is heated at 150° C. for 3 h. The reaction mixture is cooled to room temperature, aqueous hydrochloric acid is added, and thereafter extracted with ethyl acetate. From the extract is obtained after evaporation to dryness and crystallization from pyridine N-phenyl-1,2-dihydro-4-hydroxy-1-methyl-2-oxo-quinoline-3-carboxamide (1) (the same compound as 1:1). M.p. 199°–200° C.

EXAMPLE 5

A mixture of one part of N-phenyl-1,2-dihydro-4-methoxy-1-methyl-2-oxo-quinoline-3-carboxamide (prepared according to Example 6) and 5 parts of 5 molar aqueous hydrochloric acid is refluxed for 2.5 h, cooled to room temperature and then neutralized with aqueous sodium hydroxide solution. The crystalline product obtained is filtered off and recrystallized from pyridine to give N-phenyl-1,2-dihydro-4-hydroxy-1-methyl-2-oxo-quinoline-3-carboxamide (1) (the same compound as 1:1). M.p. 199°–200° C.

The same result is obtained if in the example given above the 5 molar aqueous hydrochloric acid solution is replaced by 63% aqueous hydrobromic acid solution.

The same result is also obtained if one part of N-phenyl-1,2-dihydro-4-methoxy-1-methyl-2-oxo-quinoline-3-carboxamide is refluxed with 5 parts of aqueous 5 molar sodium hydroxide solution for 1 h and the reaction mixture is neutralized with aqueous hydrochloric acid and worked up as described above.

EXAMPLE 6

A mixture of 20 parts of 1,2-dihydro-4-chloro-1-methyl-2-oxo-quinoline-3-carboxylic acid methyl ester (see Example 4), 5.2 parts of sodium methoxide, and 200 parts of methanol is stirred at 40° C. for 3 h and then allowed to cool to room temperature and filtered. The filtrate is evaporated to dryness in vacuo, and the residue is dissolved in methylene chloride and extracted with aqueous 2M sodium hydroxide solution and with ice-water. The methylene chloride solution is evaporated to dryness in vacuo. The residue solidifies and consists of 1,2-dihydro-4-methoxy-1-methyl-2-oxo-quinoline-3-carboxylic acid methyl ester. M.p. 80° C.

A mixture consisting of 12.3 parts of 1,2-dihydro-4-methoxy-1-methyl-2-oxo-quinoline-3-carboxylic acid methyl ester, 2 parts of sodium hydroxide, 2.5 parts of water, and 50 parts of dioxane is refluxed for 2.5 h. The precipitate formed is filtered off and dissolved in water. The aqueous solution is washed with methylene chloride and then acidified with aqueous hydrochloric acid. The precipitate formed consists of 1,2-dihydro-4-methoxy-1-methyl-2-oxo-quinoline-3-carboxylic acid. M.p. 177° C.

A solution of 4.7 part of 1.2-dihydro-4-methoxy-1-methyl-2-oxo-quinoline-3-carboxylic acid, 4.2 parts of triethylamine in 45 parts of chloroform is cooled to −6° C., and a solution of 2.6 parts of thionyl chloride in 9 parts of chloroform is added dropwise with stirring. The temperature is allowed to rise to 0° C., and after 1 h 2.1 parts of aniline are added dropwise.

The reaction mixture is allowed to warm up to room temperature and is then extracted with water and aqueous sodium hydrogen carbonate solution. The chloroform solution is evaporated to dryness in vacuo, and the residue is crystallized from butanone to give N-phenyl-1,2-dihydro-4-methoxy-1-methyl-2-oxo-quinoline-3-carboxamide (1). M.p. 232°–4° C.

In essentially the same manner the following compounds are obtained from the corresponding starting materials.
2. N-phenyl-4-n-butoxy-1,2-dihydro-1-methyl-2-oxo-quinoline-3-carboxamide.
3. N-(4-dimethylaminophenyl)-1,2-dihydro-4-methoxy-1-methyl-2-oxo-quinoline-3-carboxamide, m.p. 217° C.
4. N-methyl-N-phenyl-1,2-dihydro-4-methoxy-1-methyl-2-oxo-quinoline-3-carboxamide, m.p. 211° C.
5. N-methyl-N-(4-methylaminophenyl)-4-n-butoxy-1,2-dihydro-1-isobutyl-2-oxo-quinoline-3-carboxamide, and
6 N-ethyl-N-2-pyridyl-1,2-dihydro-6-dimethylamino-4-methoxy-1-methyl-2-oxo-quinoline-3-carboxamide.

EXAMPLE 7

A mixture of 1,2-dihydro-4-hydroxy-1-methyl-2-oxo-quinoline-3-carboxylic acid methyl ester (5 parts), 2-aminothiazole (2.5 parts), and pyridine (20 parts) is heated at 125° C. for 4 h. The methanol formed is distilled off continuously. The product, N-(2-thiazolyl)-1,2-dihydro-4-hydroxy-1-methyl-2-oxo-quinoline-3-carboxamide (1), precipitates on cooling to room temperature and is filtered off and recrystallized from pyridine. M.p. 251°–3° C.

In essentially the same manner the following compounds are obtained from the corresponding starting materials.
2. N-/2-pyridyl/-1,2-dihydro-4-hydroxy-1-methyl-2-oxo-quinoline-3-carboxamide, m.p. 180°–1° C.
3. N-/2-(4-methyl-thiazolyl)/-1,2-dihydro-4-hydroxy-1-methyl-2-oxo-quinoline-3-carboxamide, m.p. 206° C.
4. N-pyrazinyl-1,2-dihydro-4-hydroxy-1-methyl-2-oxo-quinoline-3-carboxamide, m.p. 218°–20° C.
5. N-/2-pyrimidinyl/-1,2-dihydro-4-hydroxy-1-methyl-2-oxo-quinoline-3-carboxamide, m.p. 220°–2° C.
6. N-/2-pyridyl/-1,2-dihydro-4-hydroxy-1-isopropyl-2-oxo-quinoline-3-carboxamide, m.p. 209° C.
7. N-/2-pyridyl/-1,2-dihydro-4-hydroxy-1-isobutyl-2-oxo-quinoline-3-carboxamide, m.p. 167° C.
8. N-/2-thiazolyl/-1,2-dihydro-4-hydroxy-1-isobutyl-2-oxo-quinoline-3-carboxamide, m.p. 239° C.

9. N-/2-thiazolyl/-1,2-dihydro-4-hydroxy-1-isopropyl-2-oxo-quinoline-3-carboxamide, m.p. 231° C.
10. N-/2-pyridyl/-1,2-dihydro-4-hydroxy-2-oxo-1-n-propyl-quinoline-3-carboxamide, m.p. 181° C.
11. N-/2-thiazolyl/-1,2-dihydro-4-hydroxy-2-oxo-1-n-propyl-quinoline-3-carboxamide, m.p. 211° C.
12. N-(3-pyridyl)-1,2-dihydro-4-hydroxy-1-methyl-2-oxo-quinoline-3-carboxamide, m.p. 215° C.
13. N-(4-pyridyl)-6-n-butyl-1,2-dihydro-4-hydroxy-1-methyl-2-oxo-quinoline-3-carboxamide.
14. N-(5-chloro-2-pyridyl)-1,2-dihydro-4-hydroxy-1-methyl-2-oxo-quinoline-3-carboxamide.
15. N-(2-methoxy-5-pyridyl)-6-n-butoxy-1,2-dihydro-4-hydroxy-1-methyl-2-oxo-quinoline-3-carboxamide.
16. N-(4,6-dimethyl-2-pyridyl)-1,2-dihydro-4-hydroxy-1-methyl-2-oxo-quinoline-3-carboxamide.
17. N-(4-methyl-2-thiazolyl)-6-chloro-1,2-dihdro-4-hydroxy-1-methyl-2-oxo-quinoline-3-carboxamide.
18. N-(5-chloro-2-thiazolyl)-1,2-dihydro-5-fluoro-4-hydroxy-1-methyl-2-oxo-quinoline-3-carboxamide.
19. N-pyrazinyl-1-allyl-1,2-dihydro-4-hydroxy-2-oxo-quinoline-3-carboxamide, m.p. 230°-232° C.
20. N-(2-thiazolyl)-1,2-dihydro-4-hydroxy-1-methyl-2-oxo-5-nitro-quinoline-3-carboxamide.
21. N-(2-pyridyl)-1,2-dihydro-6-dimethylamino-4-hydroxy-1-methyl-2-oxo-quinoline-3-carboxamide.
22. N-(3-pyridazinyl)-6-n-butylamino-1,2-dihydro-1-ethyl-4-hydroxy-2-oxo-quinoline-3-carboxamide.
23. N-(2-thiazolyl)-6-acetylamino-1,2-dihydro-1-ethyl-4-hydroxy-2-oxo-quinoline-3-carboxamide.
24. N-(2-imidazolyl)-1,2-dihydro-4-hydroxy-1-methyl-2-oxo-quinoline-3-carboxamide, hydrochloride, m.p. 287° C.
25. N-(3-methyl-5-isothiazolyl)-1,2-dihydro-1-(4-chlorophenyl)-4-hydroxy-6,7-methylenedioxy-2-oxo-quinoline-3-carboxamide.
26. N-(4-imidazolyl)-1,2-dihydro-1-(4-methoxyphenyl)-4,6-dihydroxy-2-oxo-quinoline-3-carboxamide.
27. N-(3-pyrazolyl)-1-cyclohexyl-1,2-dihydro-4-hydroxy-2-oxo-quinoline-3-carboxamide.
28. N-(3-methyl-5-isothiazolyl)-1,2-dihydro-4-hydroxy-1-methyl-2-oxo-quinoline-3-carboxamide, m.p. 274° C.
29. N-/4-(2,6-dimethylpyrimidyl)/-1,2-dihydro-4-hydroxy-1-methyl-2-oxo-quinoline-3-carboxamide, m.p. 260° C.
30. N-/5-(2-methoxypyridyl)/-1,2-dihydro-4-hydroxy-1-methyl-2-oxo-quinoline-3-carboxamide, m.p. 210° C., and
31. N-/2-(4,5-dihydrothiazolyl)/-1,2-dihydro-4-hydroxy-1-methyl-2-oxo-quinoline-3-carboxamide

EXAMPLE 8

A mixture consisting of 34.5 parts of N-(4-nitrophenyl)-1,2-dihydro-4-hydroxy-1-methyl-2-oxo-quinoline-3-carboxamide (1:20), 0.3 parts of platinic oxide, and 330 parts of toluene is hydrogenated at 50° C. and at 5 atm. The catalyst is filtered off and the filtrate is evaporated to dryness in vacuo. The residue crystallizes to give N-(4-aminophenyl)-1,2-dihydro-4-hydroxy-1-methyl-2-oxo-quinoline-3-carboxamide (1). M.p. 300° C.

2. N-phenyl-5-amino-1,2-dihydro-4-hydroxy-1-methyl-2-oxo-quinoline-3-carboxamide, m.p. 219° C. (from compound 1:42)
3. N-(4-aminophenyl)-N-methyl-1,2-dihydro-4-hydroxy-1-methyl-2-oxo-quinoline-3-carboxamide (from compound 20:42)
4. N-methyl-N-phenyl-5-amino-1,2-dihydro-4-hydroxy-1-methyl-2-oxo-quinoline-3-carboxamide (from compound 20:36)
5. N-(2-thiazolyl)-5-amino-1,2-dihydro-4-hydroxy-1-methyl-2-oxo-quinoline-3-carboxamide (from compound 7:20), and
6. N-methyl-N-(2-thiazolyl)-5-amino-1,2-dihydro-4-hydroxy-1-methyl-2-oxo-quinoline-3-carboxamide (from compound 20:70)

EXAMPLE 9

A mixture of 2 parts of N-(4-aminophenyl)-1,2-dihydro-4-hydroxy-1-methyl-2-oxo-quinoline-3-carboxamide, 5 parts of pyridine, and 10 parts of acetic anhydride is left overnight at room temperature. Water is added and the precipitate is filtered off and washed with 2M aqueous hydrochloric acid, water, methanol and ethylether to give N-(4-acetylaminophenyl)-1,2-dihydro-4-hydroxy-1-methyl-2-oxo-quinoline-3-carboxamide (1). M.p. 231°-4° C. (The same compound as 1:41.)

In essentially the same manner the following compounds are obtained from the corresponding starting materials:

2. N-methyl-N-phenyl-4-acetylamino-1,2-dihydro-1-methyl-2-oxo-quinoline-3-carboxamide (from compound 10:5)
3. N-methyl-N-phenyl-4-(N-acetyl-N-methylamino)-1,2-dihydro-1-methyl-2-oxo-quinoline-3-carboxamide (from compound 10:6) and
4. N-methyl-N-phenyl-4-acetoxy-1,2-dihydro-1-methyl-2-oxo-quinoline-3-carboxamide, m.p. 260° C. (from compound 1:43)

EXAMPLE 10

A reaction mixture consisting of N-phenyl-4-chloro-1,2-dihydro-1-methyl-2-oxo-quinoline-3-carboxamide (12 parts), concentrated aqueous ammonia (25 parts), and methanol (60 parts) is heated in an autoclave at 100° C. for 48 hours. After cooling to room temperature the precipitate formed is filtered off and recrystallized from pyridine and dried to give N-phenyl-4-amino-1,2-dihydro-1-methyl-2-oxo-quinoline-3-carboxamide (1). M.p. 248° C.

In essentially the same manner the following compounds are obtained from the corresponding starting materials.

2. N-phenyl-1,2-dihydro-1-methyl-4-methylamino-2-oxo-quinoline-3-carboxamide.
3. N-phenyl-1,2-dihydro-4-dimethylamino-1-methyl-2-oxo-quinoline-3-carboxamide.
4. N-phenyl-4-n-butylamino-1,2-dihydro-1-methyl-2-oxo-quinoline-3-carboxamide.
5. N-methyl-N-phenyl-4-amino-1,2-dihydro-1-methyl-2-oxo-quinoline-3-carboxamide, m.p. 227° C.
6. N-methyl-N-phenyl-1,2-dihydro-1-methyl-4-methylamino-2-oxo-quinoline-3-carboxamide, m.p. 250° C.
7. N-methyl-N-phenyl-1,2-dihydro-4-dimethylamino-1-methyl-2-oxo-quinoline-3-carboxamide, m.p. 169° C.
8. N-methyl-N-phenyl-1,2-dihydro-6-methoxy-1-methyl-4-methylamino-2-oxo-quinoline-3-carboxamide
9. N-methyl-N-phenyl-7-chloro-1,2-dihydro-1-methyl-4-methylamino-2-oxo-quinoline-3-carboxamide
10. N-methyl-N-phenyl-1-allyl-4-amino-1,2-dihydro-2-oxo-quinoline-3-carboxamide
11. N-methyl-N-phenyl-1,2-dihydro-1,6-dimethyl-4-dimethylamino-2-oxo-quinoline-3-carboxamide 12. N-(4-methoxyphenyl)-N-methyl-4-amino-1,2-dihydro-1-methyl-2-oxo-quinoline-2-carboxamide
13. N-(4-chlorophenyl)-N-methyl-4-amino-1,2-dihydro-1-methyl-2-oxo-quinoline-3-carboxamide
14. N-(2-thiazolyl)-4-amino-1,2-dihydro-1,8-ethylene-2-oxo-quinoline-3-carboxamide
15. N-pyrazinyl-1,2-dihydro-4-methylamino-2-oxo-1,8-trimethylene-quinoline-3-carboxamide
16. N-(2-pyridyl)-1,2-dihydro-4-dimethylamino-1,8-ethylene-2-oxo-quinoline-3-carboxamide
17. N-methyl-N-(2-thiazolyl)-4-amino-1,2-dihydro-1-methyl-2-oxo-quinoline-3-carboxamide
18. N-methyl-N-(2-pyridyl)-1,2-dihydro-1-methyl-4-methylamino-2-oxo-quinoline-3-carboxamide
19. N-methyl-N-pyrazinyl-1,2-dihydro-4-dimethylamino-1-methyl-2-oxo-quinoline-3-carboxamide
20. N-phenyl-4-amino-1,2-dihydro-1,8-ethylene-2-oxo-quinoline-3-carboxamide
21. N-phenyl-1,2-dihydro-4-methylamino-2-oxo-1,8-trimethylene-quinoline-3-carboxamide, and
22. N-(4-dimethylaminophenyl)-1,2-dihydro-4-dimethylamino-1,8-ethylene-2-oxo-quinoline-3-carboxamide

EXAMPLE 11

A reaction mixture consisting of N-methyl-isatoic anhydride (18 parts), N-phenyl-cyano-acetamide (18 parts), pyridine (100 parts), and triethylamine (10 parts) is stirred at room temperature for five days. Water is added and the precipitate formed is removed by filtration. The filtrate is acidified and extracted with methylene chloride. After drying and evaporation to dryness in vacuo the extract gives a crystalline residue which consists of N-phenyl-1,2-dihydro-4-hydroxy-2-imino-1-methyl-quinoline-3-carboxamide (1). M.p. 275°–277° C.

In essentially the same manner the following compounds are obtained from the corresponding starting materials.
2. N-phenyl-6-chloro-1,2-dihydro-4-hydroxy-2-imino-1-methyl-quinoline-3-carboxamide, and
3. N-(4-chlorophenyl)-1,2-dihydro-4-hydroxy-2-imino-1-methyl-quinoline-3-carboxamide.

EXAMPLE 12

A mixture of 1,2-dihydro-1,8-ethylene-4-hydroxy-2-oxo-quinoline-3-carboxylic acid ethyl ester (10 parts), aniline (5 parts), and pyridine (40 parts) is heated at 125° C. for 3 h. The ethanol formed is distilled off continuously. The product, N-phenyl-1,2-dihydro-1,8-ethylene-4-hydroxy-2-oxo-quinoline-3-carboxamide (1) (the same compound as 2:2), precipitates on cooling to room temperature and is filtered off and recrystallized from pyridine. M.p. 215°–17° C.

In essentially the same manner the following compounds are obtained from the corresponding starting materials.
2. N-(4-chlorophenyl)-1,2-dihydro-1,8-ethylene-4-hydroxy-6-methyl-2-oxo-quinoline-3-carboxamide
3. N-(4-dimethylaminophenyl)-1,2-dihydro-1,8-ethylene-4-hydroxy-6-methoxy-2-oxo-quinoline-3-carboxamide
4. N-(3-butylthiophenyl)-1,2-dihydro-6,7-dimethoxy-1,8-ethylene-4-hydroxy-2-oxo-quinoline-3-carboxamide.
5. N-(4-hydroxyphenyl)-1,2-dihydro-1,8-ethylene-6-fluoro-4-hydroxy-2-oxo-quinoline-3-carboxamide
6. N-(4-carboxymethylphenyl)-1,2-dihydro-1,8-ethylene-4-hydroxy-2-oxo-quinoline-3-carboxamide, calcium salt
7. N-(4-pyrrolidinophenyl)-1,2-dihydro-1,8-ethylene-4-hydroxy-2-oxo-quinoline-3-carboxamide, hydrochloride, and
8. N-(4-dimethylaminophenyl)-1,2-dihydro-1,8-ethylene-4-hydroxy-2-oxo-quinoline-3-carboxamide, m.p. 230° C.

EXAMPLE 13

A mixture of 1,2-dihydro-4-hydroxy-2-oxo-1,8-trimethylene-quinoline-3-carboxylic acid ethyl ester (10 parts), aniline (5 parts), and pyridine (40 parts) is heated at 125° C. for 3 h. The ethanol formed is distilled off continously. The product, N-phenyl-1,2-dihydro-4-hydroxy-2-oxo-1,8-trimethylene-quinoline-3-carboxamide (1) (the same compound as 2:3), precipitates on cooling to room temperature and is filtered off and recrystallized from pyridine. M.p. 177°–8° C.

In essentially the same manner the following compounds are obtained from the corresponding starting materials.
2. N-(4-n-pentanoyloxyphenyl)-6-chloro-1,2-dihydro-4-hydroxy-2-oxo-1,8-trimethylene-quinoline-3-carboxamide
3. N-(4-dimethylaminophenyl)-1,2-dihydro-6-dimethylamino-4-hydroxy-2-oxo-1.8-trimethylene-quinoline-3-carboxamide
4. N-(4-n-butylaminophenyl)-6-i-butyrylamino-1,2-dihydro-4-hydroxy-2-oxo-1,8-trimethylene-quinoline-3-carboxamide
5. N-(4-acetylaminophenyl)-1,2-dihydro-4-hydroxy-6,7-methylenedioxy-2-oxo-1,8-trimethylene-quinoline-3-carboxamide
6. N-(4-carboxymethyloxyphenyl)-1,2-dihydro-4,6-dihydroxy-2-oxo-1,8-trimethylene-quinoline-3-carboxamide, sodium salt, and
7. N-(4-dimethylaminophenyl)-1,2-dihydro-4-hydroxy-2-oxo-1,8-trimethylene-quinoline-3-carboxamide, m.p. 208° C.

EXAMPLE 14

A mixture of 1,2-dihydro-1,8-ethylene-4-hydroxy-2-oxo-quinoline-3-carboxylic acid ethyl ester (10 parts), aniline (4 parts), and pyridine (40 parts) is heated at 125° C. for 3 h. The ethanol formed is distilled off continuously. The product, N-phenyl-1,2-dihydro-1,8-ethylene-4-hydroxy-2-oxo-quinoline-3-carboxamide (1) (the same compound as 2:2), precipitates on cooling to room temperature and is filtered off. M.p. 215°–17° C.

In substantially the same manner the following compounds are obtained from the corresponding starting materials.
2. N-(3-pyridyl)-1,2-dihydro-1,8-ethylene-4-hydroxy-6-methyl-2-oxo-quinoline-3-carboxamide.
3. N-(4-pyridyl)-6-n-butyl-1,2-dihydro-4-hydroxy-2-oxo-1,8-trimethylene-quinoline-3-carboxamide.
4. N-(5-chloro-2-pyridyl)-1,2-dihydro-6,7-dimethoxy-1,8-ethylene-4-hydroxy-2-oxo-quinoline-3-carboxamide.
5. N-(2-methoxy-5-pyridyl)-1,2-dihydro-6-fluoro-4-hydroxy-2-oxo-1,8-trimethylene-quinoline-3-carboxamide.
6. N-(4,6-dimethyl-2-pyridyl)-6-chloro-1,2-dihydro-1,8-ethylene-4-hydroxy-2-oxo-quinoline-3-carboxamide.

7. N-(4-methyl-2-thiazolyl)-1,2-dihydro-6-dimethylamino-4-hydroxy-2-oxo-1,8-trimethylene-quinoline-3-carboxamide.
8. N-(5-chloro-2-thiazolyl)-1,2-dihydro-6-i-butyrylamino-1,8-ethylene-4-hydroxy-2-oxo-quinoline-3-carboxamide.
9. N-pyrazinyl-1,2-dihydro-1,8-ethylene-4-hydroxy-2-oxo-quinoline-3-carboxamide, m.p. 244° C.
10. N-(2-pyridyl)-1,2-dihydro-1,8-ethylene-4-hydroxy-2-oxo-quinoline-3-carboxamide.
11. N-(2-thiazolyl)-1,2-dihydro-4-hydroxy-2-oxo-1,8-trimethylene-quinoline-3-carboxamide.
12. N-(3-pyridazinyl)-1,2-dihydro-4,6-dihydroxy-1,8-ethylene-2-oxo-quinoline-3-carboxamide.
13. N-(2-pyrimidinyl)-1,2-dihydro-4-hydroxy-2-oxo-1,8-trimethylen-quinoline-3-carboxamide.
14. N-(2-imidazolyl)-1,2-dihydro-1,8-ethylene-4-hydroxy-2-oxo-quinoline-3-carboxamide.
15. N-(3-methyl-5-isothiazolyl)-1,2-dihydro-4-hydroxy-2-oxo-1,8-trimethylene-quinoline-3-carboxamide.
16. N-(4-imidazolyl)-1,2-dihydro-1,8-ethylene-4-hydroxy-2-oxo-quinoline-3-carboxamide, and
17. N-pyrazinyl-1,2-dihydro-4-hydroxy-2-oxo-1,8-trimethylene-quinoline-3-carboxamide, m.p. 243° C.

EXAMPLE 15

To a mixture of 27 parts of N-phenylcarbamoyl acetic acid ethyl ester in 75 parts of dimethylformamide are added 5.3 parts of a 60% suspension of sodium hydride in mineral oil. The mixture is heated at 80° C. for 15 minutes. A solution of 22 parts of N-methyl isatoic anhydride (=1-methyl-2H-3,1-benzoxazine-2,4(1H)(dione) in 125 parts of dimethylformamide is added. The reaction mixture is then heated at 110° C. for 30 minutes and cooled to room temperature. The crystalline precipitate is filtered off and washed with water, methanol, and ethyl ether and consists of N-phenyl-1,2-dihydro-4-hydroxy-1-methyl-2-oxo-quinoline-3-carboxamide sodium salt (1).

EXAMPLE 16

The general method described in Example 6 above is used for the preparation of the following compounds from the corresponding starting materials.
1. N-(2-thiazolyl)-1,2-dihydro-1,8-ethylene-4-methoxy-2-oxo-quinoline-3-carboxamide
2. N-pyrazinyl-1,2-dihydro-4-methoxy-2-oxo-1,8-trimethylene-quinoline-3-carboxamide, and
3. N-(2-pyridyl)-4-n-butoxy-1,2-dihydro-1,8-ethylene-2-oxo-quinoline-3-carboxamide

EXAMPLE 17

The general method described in Example 6 above is used for the preparation of the following compounds from the corresponding starting materials.
1. N-(2-thiazolyl)-1,2-dihydro-4-methoxy-1-methyl-2-oxo-quinoline-3-carboxamide, and
2. N-(2-pyridyl)-1,2-dihydro-4-i-butoxy-1-methyl-2-oxo-quinoline-3-carboxamide

EXAMPLE 18

The general method described in Example 6 above is used for the preparation of the following compounds from the corresponding starting materials.
1. N-phenyl-1,2-dihydro-1,8-ethylene-4-methoxy-2-oxo-quinoline-3-carboxamide
2. N-phenyl-1,2-dihydro-4-methoxy-2-oxo-1,8-trimethylene-quinoline-3-carboxamide, and
3. N-(4-dimethylaminophenyl)-1,2-dihydro-4-ethoxy-1,8-ethylene-2-oxo-quinoline-3-carboxamide

EXAMPLE 19

A reaction mixture consisting of N-methyl malonanilic acid methyl ester (13 parts), sodium methoxide (4,2 parts) and dimethyl formamide (62 parts) is heated to 100° C. under vacuum for 40 minutes and methanol formed is distilled off, whereafter 1,8-trimethylene-isatoic anhydride (=6,7-dihydro-1H,3H,5H-pyrido(3,2,1-ij)(3,1)-benzoxazine-1,3-dione) (6,4 parts) is added at 80° C. The reaction mixture is then heated at 110° C. while stirring under vacuum for 40 minutes. Water is added after cooling to room temperature, and the solution so obtained is extracted with ethyl ether. The aqueous phase is acidified with hydrochloric acid solution and extracted with methylene chloride. The extract is washed with water, dried and evaporated to dryness. The crystalline residue is washed with acetone and, dried, consists of N-methyl-N-phenyl-1,2-dihydro-4-hydroxy-2-oxo-1,8-trimethylene-quinoline-3-carboxamide (1). M.p. 234° C.

In essentially the same manner the following compounds are obtained from the corresponding starting materials.
2. N-(4-fluorophenyl)-N-methyl-1,2-dihydro-hydroxy-2-oxo-1,8-trimethylene-quinoline-3-carboxamide, and
3. N-allyl-N-(3,4-dimethoxyphenyl)-1,2-dihydro-4-hydroxy-2-oxo-1,8-trimethylene-quinoline-3-carboxamide

EXAMPLE 20

Phosphorous trichloride (1.73 parts) is added dropwise to a solution of 8.1 parts of N-methylaniline in 40 parts of dry toluene while stirring the reaction mixture. Stirring is continued at room temperature for 30 minutes, whereafter 6.15 parts of 1,2-dihydro-4-hydroxy-1-allyl-2-oxo-quinoline-3-carboxylic acid are added. The reaction mixture is heated at 100° C. for two hours and then cooled down.

The reaction mixture is extracted with a 2M sodium hydroxide solution and the extract obtained is neutralized and clarified by filtration.

The filtrate is acidified and the precipitate formed is filtered off and dissolved in methylene chloride and the solution is clarified by filtration and evaporated to dryness. The crystalline residue is washed with acetone and dried.

The product so obtained consists of N-methyl-N-phenyl-1,2-dihydro-1-allyl-4-hydroxy-2-oxo-quinoline-3-carboxamide, (1). M.p. 204° C.

In essentially the same manner the following compounds are obtained from the corresponding starting materials.
2. N-methyl-N-phenyl-7-chloro-1,2-dihydro-4-hydroxy-1-methyl-2-oxo-quinoline-3-carboxamide, m.p. 193° C.
3. N-methyl-N-phenyl-1,2-dihydro-6-dimethylamino-4-hydroxy-1-methyl-2-oxo-quinoline-3-carboxamide, m.p. >300° C.
4. N-(4-chloro-phenyl)-N-methyl-1,2-dihydro-4-hydroxy-6-methoxy-1-methyl-2-oxo-quinoline-3-carboxamide, m.p. 197° C.
5. N-methyl-N-phenyl-1,2-dihydro-4-hydroxy-6-methoxy-1-methyl-2-oxo-quinoline-3-carboxamide, m.p. 240° C.

6. N-(4-methoxyphenyl)-N-methyl-1,2-dihydro-4-hydroxy-6-methoxy-1-methyl-2-oxo-quinoline-3-carboxamide, m.p. 220° C.
7. N-1-diphenyl-N-methyl-1,2-dihydro-4-hydroxy-2-oxo-quinoline-3-carboxamide
8. N-methyl-N-phenyl-1,2-dihydro-4,6-dihydroxy-1-methyl-2-oxo-quinoline-3-carboxamide
9. N-(4-piperidinophenyl)-N-methyl-1,2-dihydro-4-hydroxy-1-methyl-2-oxo-quinoline-3-carboxamide
10. N-methyl-N-phenyl-1,2-dihydro-1-ethyl-4-hydroxy-2-oxo-quinoline-3-carboxamide
11. N-/4-carboxymethylphenyl/-N-methyl-1,2-dihydro-4-hydroxy-1-methyl-2-oxo-quinoline-3-carboxamide
12. N-methyl-N-phenyl-1,2-dihydro-4-hydroxy-1-isopropyl-2-oxo-quinoline-3-carboxamide
13. N-methyl-N-phenyl-1,2-dihydro-4-hydroxy-1-isobutyl-2-oxo-quinoline-3-carboxamide
14. N-methyl-N-phenyl-1,2-dihydro-4-hydroxy-2-oxo-1-n-propyl-quinoline-3-carboxamide
15. N-methyl-N-phenyl-6-chloro-1,2-dihydro-4-hydroxy-1-methyl-2-oxo-quinoline-3-carboxamide
16. N-methyl-N-phenyl-1,2-dihydro-5-fluoro-4-hydroxy-1-methyl-2-oxo-quinoline-3-carboxamide
17. N-methyl-N-phenyl-5-dimethylamino-1,2-dihydro-4-hydroxy-1-methyl-2-oxo-quinoline-3-carboxamide
18. N-methyl-N-/4-methylaminophenyl/-1,2-dihydro-4-hydroxy-1-methyl-2-oxo-quinoline-3-carboxamide
19. N-methyl-N-phenyl-1,2-dihydro-4-hydroxy-8-methoxy-1-methyl-2-oxo-quinoline-3-carboxamide
20. N-methyl-N-/4-diethylaminophenyl/-1,2-dihydro-4-hydroxy-1-methyl-2-oxo-quinoline-3-carboxamide
21. N-methyl-N-/4-pyrrolidinophenyl/-1,2-dihydro-4-hydroxy-1-methyl-2-oxo-quinoline-3-carboxamide
22. N-(3-n-butylthiophenyl)-N-methyl-6-n-butoxy-1,2-dihydro-4-hydroxy-1-methyl-2-oxo-quinoline-3-carboxamide
23. N-(4-bromophenyl)-N-methyl-1,2-dihydro-4-hydroxy-1-methyl-2-oxo-quinoline-3-carboxamide
24. N-(3-cyanophenyl)-N-methyl-6-bromo-1,2-dihydro-1-ethyl-4-hydroxy-2-oxo-quinoline-3-carboxamide
25. N-methyl-N-(4-methylsulphonylphenyl)-1,2-dihydro-1-ethyl-4-hydroxy-2-oxo-quinoline-carboxamide
26. N-/4-(N-n-butyl-N-n-propyl-amino)phenyl-N-methyl-6-acetoxy-1,2-dihydro-1-ethyl-4-hydroxy-2-oxo-quinoline-3-carboxamide
27. N-(4-carboxyphenyl)-N-methyl-6-n-butylamino-1,2-dihydro-4-hydroxy-1-methyl-2-oxo-quinoline-3-carboxamide, sodium salt
28. N-(3-i-butyrylphenyl)-N-methyl-6-acetylamino-1,2-dihydro-4-hydroxy-1-methyl-2-oxo-quinoline-3-carboxamide
29. N-methyl-N-(3,4-methylenedioxyphenyl)-1,2-dihydro-4-hydroxy-1-methyl-2-oxo-quinoline-3-carboxamide
30. N-methyl-N-(4-piperidinophenyl)-1,2-dihydro-4-hydroxy-1-methyl-6,7-methylenedioxy-2-oxo-quinoline-3-carboxamide, hydrochloride
31. N-(4-n-butylaminophenyl)-N-methyl-1,2-dihydro-4,6-dihydroxy-1-methyl-2-oxo-quinoline-3-carboxamide
32. N-(4-ethoxycarbonylmethylphenyl)-N-methyl-1-cyclohexyl-1,2-dihydro-4-hydroxy-2-oxo-quinoline-3-carboxamide
33. N-methyl-N-phenyl-1-(4-chlorophenyl)-1,2-dihydro-4-hydroxy-2-oxo-quinoline-3-carboxamide
34. N-methyl-N-phenyl-1-(4-methoxyphenyl)-1,2-dihydro-4-hydroxy-2-oxo-quinoline-3-carboxamide
35. N-(4-acetylaminophenyl)-N-methyl-1,2-dihydro-4-hydroxy-1-methyl-2-oxo-quinoline-3-carboxamide
36. N-methyl-N-phenyl-1,2-dihydro-4-hydroxy-1-methyl-5-nitro-2-oxo-quinoline-3-carboxamide
37. N-phenyl-N-methyl-1,2-dihydro-4-hydroxy-1-methyl-2-oxo-quinoline-3-carboxamide, m.p. 200°–204° C.
38. N-methyl-N-phenyl-1,2-dihydro-1,6-dimethyl-4-hydroxy-2-oxo-quinoline-3-carboxamide
39. N-(4-dimethylaminophenyl)-N-methyl-1-allyl-1,2-dihydro-4-hydroxy-2-oxo-quinoline-3-carboxamide
40. N-(4-acetylphenyl)-N-methyl-1,2-dihydro-4-hydroxy-1-methyl-2-oxo-quinoline-3-carboxamide
41. N-methyl-N-(3-methylmercaptophenyl)-1,2-dihydro-4-hydroxy-1-methyl-2-oxo-quinoline-3-carboxamide
42. N-methyl-N-/4-nitrophenyl/-1,2-dihydro-4-hydroxy-1-methyl-2-oxo-quinoline-3-carboxamide
43. N-(3-hydroxyphenyl)N-methyl-1,2-dihydro-4-hydroxy-1-methyl-2-oxo-quinoline-3-carboxamide
44. N-(4-carboxymethylphenyl)N-methyl-1,2-dihydro-6,7-dimethoxy-4-hydroxy-1-methyl-2-oxo-quinoline-3-carboxamide
45. N-(4-carboxymethoxyphenyl)-N-methyl-6-n-butyl-1,2-dihydro-4-hydroxy-1-methyl-2-oxo-quinoline-3-carboxamide
46. N-(4-methoxycarbonylmethoxyphenyl)-N-methyl-1,2-dihydro-4-hydroxy-1-methyl-2-oxo-quinoline-3-carboxamide
47. N-(4-methoxycarboxylmethyl-phenyl)-N-methyl-1,2-dihydro-6-dimethylamino-1-ethyl-4-hydroxy-2-oxo-quinoline-3-carboxamide
48. N-(4-acetoxyphenyl)-N-methyl-1,2-dihydro-4-hydroxy-1-methyl-2-oxo-quinoline-3-carboxamide
49. N-(4-ethylaminophenyl)-N-methyl-1,2-dihydro-4-hydroxy-1-methyl-2-oxo-quinoline-3-carboxamide
50. N-methyl-N-(4-pivaloyloxyphenyl)-1,2-dihydro-4-hydroxy-1-methyl-2-oxo-quinoline-3-carboxamide
51. N-ethyl-N-(2-thiazolyl)-1,2-dihydro-4-hydroxy-1-methyl-2-oxo-quinoline-3-carboxamide
52. N-propyl-N-(2-pyridyl)-1,2-dihydro-4-hydroxy-1-methyl-2-oxo-quinoline-3-carboxamide
53. N-methyl-N-/2-(4-methyl-thiazolyl)/-1,2-dihydro-4-hydroxy-1-methyl-2-oxo-quinoline-3-carboxamide
54. N-(2-methoxy-ethyl)-N-pyrazinyl-1,2-dihydro-4-hydroxy-1-methyl-2-oxo-quinoline-3-carboxamide
55. N-allyl-N-(2-pyrimidinyl)-1,2-dihydro-4-hydroxy-1-methyl-2-oxo-quinoline-3-carboxamide
56. N-methyl-N-(2-pyridyl)-1,2-dihydro-4-hydroxy-1-isopropyl-2-oxo-quinoline-3-carboxamide
57. N-methyl-N-(2-pyridyl)-1,2-dihydro-4-hydroxy-isobutyl-2-oxo-quinoline-3-carboxamide
58. N-methyl-N-(2-thiazolyl)-1,2-dihydro-4-hydroxy-1-isobutyl-2-oxo-quinoline-3-carboxamide
59. N-methyl-N-(2-thiazolyl)-1,2-dihydro-4-hydroxy-1-isopropyl-2-oxo-quinoline-3-carboxamide
60. N-methyl-N-(2-pyridyl)-1,2-dihydro-4-hydroxy-2-oxo-1-n-propyl-quinoline-3-carboxamide
61. N-methyl-N-(2-thiazolyl)-1,2-dihydro-4-hydroxy-2-oxo-1-n-propyl-quinoline-3-carboxamide
62. N-methyl-N-(3-pyridyl)-1,2-dihydro-4-hydroxy-1-methyl-2-oxo-quinoline-3-carboxamide
63. N-methyl-N-(4-pyridyl)-6-n-butyl-1,2-dihydro-4-hydroxy-1-methyl-2-oxo-quinoline-3-carboxamide
64. N-(5-chloro-2-pyridyl)-N-methyl-1,2-dihydro-4-hydroxy-1-methyl-2-oxo-quinoline-3-carboxamide 65. N-(2-methoxy-5-pyridyl)-N-methyl-6-n-butoxy-1,2-dihydro-4-hydroxy-1-methyl-2-oxo-quinoline-3-carboxamide
66. N-(4,6-dimethyl-2-pyridyl)-N-methyl-1,2-dihydro-4-hydroxy-1-methyl-2-oxo-quinoline-3-carboxamide
67. N-methyl-N-(4-methyl-2-thiazolyl)-6-chloro-1,2-dihydro-4-hydroxy-1-methyl-2-oxo-quinoline-3-carboxamide
68. N-(5-chloro-2-thiazolyl)-N-methyl-1,2-dihydro-5-fluoro-4-hydroxy-1-methyl-2-oxo-quinoline-3-carboxamide
69. N-methyl-N-pyrazinyl-1-allyl-1,2-dihydro-4-hydroxy-2-oxo-quinoline-3-carboxamide
70. N-methyl-N-(2-thiazolyl)-1,2-dihydro-4-hydroxy-1-methyl-2-oxo-5-nitro-quinoline-3-carboxamide
71. N-methyl-N-(2-pyridyl)-1,2-dihydro-6-dimethylamino-4-hydroxy-1-methyl-2-oxo-quinoline-3-carboxamide
72. N-methyl-N-(3-pyridazinyl)-6-n-butylamio-1,2-dihydro-1-ethyl-4-hydroxy-2-oxo-quinoline-3-carboxamide
73. N-methyl-N-(2-thiazolyl)-6-acetylamino-1,2-dihydro-1-ethyl-4-hydroxy-2-oxo-quinoline-3-carboxamide
74. N-(2-imidazolyl)-N-methyl-1,2-dihydro-4-hydroxy-1-methyl-2-oxo-quinoline-3-carboxamide
75. N-methyl-N-(3-methyl-5-isothiazolyl)-1,2-dihydro-1-(4-chloro-phenyl)-4-hydroxy-6,7-methylenedioxy-2-oxo-quinoline-3-carboxamide
76. N-(4-imidazolyl)-N-methyl-1,2-dihydro-1-(4-methoxyphenyl)-4,6-dihydroxy-2-oxo-quinoline-3-carboxamide
77. N-methyl-N-(3-pyrazolyl)-1-cyclopentyl-1,2-dihydro-4-hydroxy-2-oxo-quinoline-3-carboxamide
78. N-methyl-N-(3-methyl-5-isothiazolyl)-1,2-dihydro-4-hydroxy-1-methyl-2-oxo-quinoline-3-carboxamide
79. N-/4-(2,6-dimethylpyrimidyl)/-N-methyl-1,2-dihydro-4-hydroxy-1-methyl-2-oxo-quinoline-3-carboxamide, and
80. N-/5-(2-methoxypyridyl)/-N-methyl-1,2-dihydro-4-hydroxy-1-methyl-2-oxo-quinoline-3-carboxamide

EXAMPLE 21

A mixture consisting of indoline (19 parts) and methanetricarboxylic acid triethylester (37 parts) is heated at 100° C. (under vacuum) for 5 hours while the ethanol formed is distilled off. The crystalline precipitate formed is filtered off and dissolved in ethyl ether. The ethereal solution is evaporated to dryness and diphenylether (25 parts) is added to the residue and the mixture so obtained is heated at 200° C. for 8 h. After cooling to room temperature the reaction mixture is poured into aqueous sodium hydroxide solution. This mixture is washed with ethyl ether and the aqueous phase is acidified and extracted with methylene chloride.

The extract is dried and evaporated to dryness. The residue is purified by liquid chromatography to give 1,2-dihydro-1,8-ethylene-4-hydroxy-2-oxo-quinoline-3-carboxylic acid ethyl ester (1). M.p. 150° C.

The ethylester (1) described above (3,4 parts) is dissolved in a solution consisting of acetic acid (14,3 parts) and 63% aqueous hydrobromic acid (5,8 parts). The solution so obtained is heated at 120° C. for 20 minutes. After standing over night at room temperature a crystalline precipitate is formed which is filtered off. The crystals are reprecipitated by dissolving in aqueous alkali and acidification to give 1,2-dihydro-1,8-ethylene-4-hydroxy-2-oxo-quinoline-3-carboxylic acid (2). M.p. 260° C.

N,N-dicyclohexylcarbodiimide (2,6 parts) is added to a mixture consisting of 1,2-dihydro-1,8-ethylene-4-hydroxy-2-oxo-3-carboxylic acid (2) (2,3 parts), N-methylaniline (1,1 parts) and dry toluene (20 parts) while stirring. Thereafter the stirring is continued at 90° C. for one hour. The reaction mixture is cooled to room temperature and the precipitate formed is filtered off. The precipitate is extracted with 2M sodium hydroxide solution. The extract is neutralized and clarified by filtration and acidified with hydrochloric acid solution and then extracted with methylene chloride. The methylene chloride extract is dried and evaporated to dryness in vacuum. The crystalline residue is washed with acetone and dried to give N-methyl-N-phenyl-1,2-dihydro-1,8-ethylene-4-hydroxy-2-oxo-quinoline-3-carboxamide (3). M.p. 260° C.

In essentially the same manner the following compounds are obtained from the corresponding starting materials.
4. N-methyl-N-phenyl-1,2-dihydro-4-hydroxy-1-methyl-2-oxo-quinoline-3-carboxamide, m.p. 200°–204° C.
5. N-ethyl-N-phenyl-1,2-dihydro-4-hydroxy-1-methyl-2-oxo-quinoline-3-carboxamide, m.p. 163° C.
6. N-(4-methoxyphenyl)-N-methyl-1,2-dihydro-4-hydroxy-1-methyl-2-oxo-quinoline-3-carboxamide, m.p. 185° C.
7. N-methyl-N-(2-pyridyl)-1,2-dihydro-4-hydroxy-1-methyl-2-oxo-quinoline-3-carboxamide, m.p. 141° C.
8. N-(n-butyl)-N-phenyl-1,2-dihydro-4-hydroxy-1-methyl-2-oxo-quinoline-3-carboxamide, m.p. 185° C.
9. N-(4-chlorophenyl)-N-methyl-1,2-dihydro-4-hydroxy-1-methyl-2-oxo-quinoline-3-carboxamide, m.p. 212° C.
10. N-(4-dimethylaminophenyl)-N-methyl-1,2-dihydro-4-hydroxy-1-methyl-2-oxo-quinoline-3-carboxamide, dec. 195°–200° C.
11. N-(4-hydroxyphenyl)-N-methyl-1,2-dihydro-4-hydroxy-1-methyl-2-oxo-quinoline-3-carboxamide, m.p. 258° C.
12. N-allyl-N-phenyl-1,2-dihydro-4-hydroxy-1-methyl-2-oxo-quinoline-3-carboxamide, m.p. 186° C.
13. N-(4-carboxyphenyl)-N-methyl-1,2-dihydro-4-hydroxy-1-methyl-2-oxo-quinoline-3-carboxamide, m.p. 136° C.
14. N-(4-methoxyphenyl)-N-methyl-1,2-dihydro-4-hydroxy-6-methoxy-1-methyl-2-oxo-quinoline-3-carboxamide, m.p. 220° C.
15. N-(4-n-butylphenyl)-N-methyl-1,2-dihydro-6-dimethylamino-4-hydroxy-1-methyl-2-oxo-quinoline-3-carboxamide.
16. N-(3,4-dimethoxyphenyl)-N-ethyl-1,2-dihydro-5-fluoro-4-methoxy-1-methyl-2-oxo-quinoline-3-carboxamide.
17. N-(3-methoxyphenyl)-N-methyl-1,2-dihydro-4-hydroxy-1-isopropyl-6-methyl-2-oxo-quinoline-3-carboxamide.
18. N-(4-methoxyphenyl)-N-methyl-1,2-dihydro-4-hydroxy-1,5-dimethyl-2-oxo-quinoline-3-carboxamide.
19. N-methyl-N-(4-pyrrolidinophenyl)-1-(4-fluorophenyl)-1,2-dihydro-4-hydroxy-2-oxo-quinoline-3-carboxamide.
20. N-methyl-N-pyrazinyl-1,2-dihydro-1,8-ethylene-4-hydroxy-2-oxo-quinoline-3-carboxamide.
21. N-methyl-N-2-thiazolyl-1,2-dihydro-4-hydroxy-1-methyl-2-oxo-quinoline-3-carboxamide, m.p. 142° C.

22. N-methyl-N-2-pyrimidinyl-1,2-dihydro-4-hydroxy-1-methyl-2-oxo-quinoline-3-carboxamide, sodium salt
23. N-methyl-N-pyrazinyl-1,2-dihydro-4-hydroxy-1-methyl-2-oxo-quinoline-3-carboxamide, m.p. 176° C.
24. N-methyl-N-(3-methyl-5-isothiazolyl)-6-chloro-1,2-dihydro-4-hydroxy-1-methyl-2-oxo-quinoline-3-carboxamide.
25. N-methyl-N-2-pyridyl-1-n-butyl-1,2-dihydro-4-hydroxy-6-methoxy-2-oxo-quinoline-3-carboxamide.
26. N-ethyl-N-2-pyridyl-1,2-dihydro-6-dimethylamino-4-hydroxy-1-methyl-2-oxo-quinoline-3-carboxamide.
27. N-/5-(2-methoxypyridyl)/-N-methyl-1,2-dihydro-6-fluoro-4-hydroxy-1-methyl-2-oxo-quinoline-3-carboxamide.
28. N-(4-methoxyphenyl)-N-methyl-1,2-dihydro-1,8-ethylene-4-hydroxy-2-oxo-quinoline-3-carboxamide.
29. N-n-butyl-N-(4-chlorophenyl)-1,2-dihydro-1,8-ethylene-4-hydroxy-2-oxo-quinoline-3-carboxamide.
30. N-(4-dimethylaminophenyl)-N-methyl-1,2-dihydro-1,8-ethylene-4-hydroxy-2-oxo-quinoline-3-carboxamide.
31. N-methyl-N-2-thiazolyl-1,2-dihydro-1,8-ethylene-4-hydroxy-2-oxo-quinoline-3-carboxamide.
32. N-methyl-N-2-pyrimidinyl-1,2-dihydro-4-hydroxy-2-oxo-1,8-trimethylene-quinoline-3-carboxamide.
33. N-ethyl-N-2-pyridyl-1,2-dihydro-4-hydroxy-2-oxo-1,8-trimethylene-quinoline-3-carboxamide.
34. N-allyl-N-/5-(2-methoxypyridyl)/-1,2-dihydro-1,8-ethylene-4-hydroxy-2-oxo-quinoline-3-carboxamide.
35. N-(4-fluorophenyl)-N-methyl-1,2-dihydro-4-hydroxy-1-methyl-2-oxo-quinoline-3-carboxamide, m.p. 197° C.
36. N-methyl-N-phenyl-1,2-dihydro-4-hydroxy-1-methyl-2-oxo-quinoline-3-carboxamide, sodium salt.
37. N-(2-hydroxyphenyl)-N-methyl-1,2-dihydro-4-hydroxy-1-methyl-2-oxo-quinoline-3-carboxamide, m.p. 160°.
38. N-(2-methoxycarbonylphenyl)-N-methyl-1,2-dihydro-4-hydroxy-1-methyl-2-oxo-quinoline-3-carboxamide, m.p. 167° C.
39. N-(2-hydroxyethyl)-N-phenyl-1,2-dihydro-4-hydroxy-1-methyl-2-oxo-quinoline-3-carboxamide, m.p. 122° C.
40. N-(2-acetoxyethyl)-N-phenyl-1,2-dihydro-4-hydroxy-1-methyl-2-oxo-quinoline-3-carboxamide, and
41. N-(4-methoxycarbonylphenyl)-N-methyl-1,2-dihydro-4-hydroxy-1-methyl-2-oxo-quinoline-3-carboxamide, m.p. 163° C.

EXAMPLE 22

This example illustrates the effect of the compounds of the general formula I in the carrageenan edema test in rats.

A modification of a method described in (5) was used. Female Sprague-Dawley rats weighing 110–120 g was used. At least 10 animals were used in each experimental group. Foot edema was induced by injecting carrageenan in 0.9% NaCl into the plantar surface of the right hind paw of the rats.

The substances suspended in aqueous methocel solution 10 ml/kg were administered intragastrically 30 minutes before the injection of carrageenan. The control groups were given methocel solution 10 ml/kg.

Three hours after carrageenan injection the animals were killed. The hind feet were cut off and weighed. The difference in weight of the injected right paw and the uninjected left paw was called edema weight.

Some of the results obtained are given in Table 1 below. The compounds are named by a number code, a:b, as described above before Example 1.

The effect of the substances was assessed by the edema weight expressed in percent after comparison with the control groups.

TABLE 1

Carrageenan edema test in rats - preliminary results
Dose 80 mg/kg, p. o.

| Compound | Potentiation of the carrageenan edema, % |
|---|---|
| 1:1 | 40 |
| 1:2 | 61 |
| 1:3 | 41 |
| 1:5 | 28 |
| 1:8 | 21 |
| 1:9 | 48 |
| 1:10 | 68 |
| 1:11 | 76 |
| 1:12 | 29 |
| 1:15 | 30 |
| 1:17 | 43 |
| 1:18 | 36 |
| 1:19 | 67 |
| 1:21 | 22 |
| 1:22 | 58 |
| 1:23 | 29 |
| 1:43 | 84 |
| 1:45 | 47 |
| 1:46 | 32 |
| 2:2 | 43 |
| 2:3 | 61 |
| 6:1 | 60 |
| 6:3 | 32 |
| 7:1 | 84 |
| 7:2 | 44 |
| 7:3 | 47 |
| 7:4 | 34 |
| 7:10 | 24 |
| 10:1 | 36 |
| 11:1 | 46 |
| 12:8 | 51 |
| 14:9 | 21 |
| 21.6 | 38 |
| 21:9 | 52 |

The following additional compounds potentiate significantly the carrageenan edema in the foregoing test in a dose within the range 10–160 mg/kg p.o.: 8:1, 9:1, 12:7, 13:3, 14:7, 14:12, 16:1, 17:1, 18:1, 18:2, 18:3, 20:5, 20:9, 20:10, 20:16, 20:29, 20:34, 20:35, 20:39, 21:3, 21:5, 21:7, 21:8, 21:10, 21:12, 21:14, 21:16, 21:20, 21:21, 21:35.

EXAMPLE 23

This example illustrates the effect of the compounds of the general formula I in the adjuvant arthritis test in rats.

The adjuvant arthritis test in rats produces a delayed hypersensitivity reaction and can be used for a determination of variations of the delayed hypersensitivity reaction upon drug administration to the host. An increase in the extent of the delayed hypersensitivity reaction upon drug administration consequently indicates enhanced cell-mediated immunity in the host.

A modification of a method described in (12) was used. Male Lister hooded rats weighing 250–275 g were used. At least 9 animals were used in each experimental group.

A single intradermal injection of 0.5 mg/0.1 ml heat killed Mycobacterium butyricum suspended in sterile liquid paraffinum was given into the right hind foot of all rats. After this injection, day 0, the volume of the left hind paw, measured by water displacement, was followed to the end of the experiment.

The substances suspended in aqueous methocel solution 10 ml/kg were given intragastrically. The control group was given methocel solution 10 ml/kg. The different groups of animals were thus treated once daily from day −4 to day 14. The effect of the substances was assessed by the left foot volume expressed in percent after comparison with the control groups.

Some of the results are given in Table 2 below. Compounds of the general formula I are compared with the known compounds levamisole and penicillamine which are considered to have immunostimulant activities (3).

TABLE 2

Preliminary results from the adjuvant arthritis test in rats

| Compound | Dose, mg/kg p. o. | Increase of the volume of the left foot % |
|---|---|---|
| 1:1 | 40 | 41 |
| " | 20 | 50 |
| 7:1 | 40 | 35 |
| " | 20 | 44 |
| 1:11 | 40 | 45 |
| 1:43 | 10 | 48 |
| 2:2 | 40 | 40 |
| 2:3 | " | 39 |
| 6:1 | " | 34 |
| 7:4 | " | 29 |
| 21:6 | 10 | 41 |
| 21:9 | 10 | 51 |
| Penicillamine | 40 | 0 |
| Levamisole | 10 | 12 |
| " | 5 | 4 |

The following additional compounds have a significant potentiating effect in the adjuvant arthritis test in rats in a dose of 40 mg/kg p.o.: 1:2, 1:9, 1:10, 1:12, 1:19, 1:22, 13:3, 21:4, 21:5, 21:7, 21:11, 21:14, 21:17, 21:19, 21:23, 21:24, 21:26, 21:28, 21:30, 21:31, 21:33, 21:35.

The toxicity of the compunds of the general formula I is low. The LD50 values which have been determined in mice p.o. are higher than 1000 mg/kg.

The acute LD50 of levamisole in mice is 285 mg/kg p.o. (13).

This example shows that the new compounds enhance cell-mediated immunity (3).

EXAMPLE 24

This example illustrates the effect of the compounds of the general formula I in the pertussis vaccine pleurisy test.

Pertussis vaccine pleurisy is a useful test for the evaluation of the effect of chemical compounds on the immune system. Compounds which enhance the response in this delayed hypersensitivity reaction are considered to stimulate cell-mediated immunity.

A modification of a method described in (4) was used. Male Sprague-Dawley rats weighing 250-275 g were used. At least ten animals were used in each group.

Equal volumes of Freund's incomplete adjuvant and a suspension of heat killed Bordetella pertussis organisms were mixed. To sensitize animals, day 0, 0.2 ml of a mixture containing $0.036 \times 10^{10}$ organisms/ml was injected into the dorsal surface of one hind paw and one forepaw.

The animals were challenged on day 12 with 0.1 ml of a mixture containing $0.25 \times 10^{10}$ organisms/ml that was injected intrapleurally. 48 hours after challenge, day 14, the volume of the exudate in the pleural cavity was measured.

The substances suspended in aqueous methocel solution 10 ml/kg were given intragastrically once daily from day 10 to day 13. The control groups were given methocel solution 10 ml/kg.

The effect of the substances was assessed by the exudate volume expressed in percent after comparison with the control groups.

Some of the results are given in Table 3 below. The compounds of the general formula I are compared with the known compounds levamisole and penicillamine (4).

TABLE 3

Pertussis vaccine pleurisy test in rats - preliminary results
Dose 10 mg/kg, p. o.

| Compound | Enhancement of the delayed hypersensitivity reaction assessed by the exudate vol. % |
|---|---|
| 1:1 | 55 |
| 1:5 | 47 |
| 1:8 | 27 |
| 1:10 | 30 |
| 1:11 | 37 |
| 1:12 | 65 |
| 1:43 | 70 |
| 1:50 | 46 |
| 2:2 | 64 |
| 2:3 | 66 |
| 6:1 | 91 |
| 7:1 | 81 |
| 7:4 | 27 |
| 7:10 | 41 |
| 7:28 | 61 |
| 12:8 | 29 |
| 13:7 | 21 |
| 14:17 | 27 |
| 21:5 | 29 |
| 21:6 | 90 |
| 21:7 | 21 |
| 21:9 | 84 |
| 21:11 | 34 |
| Penicillamine | 17 |
| Levamisole | 13 |

The following additional compounds have a significant enhancing effect in the pertussis vaccine pleurisy test in rats in a dose of 10 mg/kg p.o.: 1:2, 1:9, 1:13, 1:19, 1:22, 9:1, 10:5, 10:6, 10:12, 10:13, 10:17, 10:20, 12:7, 13:3, 19:1, 19:2, 20:1, 20:2, 20:3, 20:4, 20:5, 20:9, 20:10, 20:16, 20:20, 20:21, 20:29, 20:34, 20:35, 20:39, 20:54, 20:74, 20:78, 21:3, 21:8, 21:10, 21:12, 21:13, 21:14, 21:16, 21:17, 21:91, 21:20, 21:21, 21:23, 21:24, 21:26, 21:28, 21:30, 21:31, 21:33, 21:35.

EXAMPLE 25

| Manufacturing process for tablets a 20 mg Model batch of 1000 tablets | | |
|---|---|---|
| I | Active Compound, mesh[+] 70 | 20 g |
|   | lactosum, Ph. Nord. | 210 g |
|   | Amylum maidis, Ph. Nord. | 75 g |
| II | Kollidon 25, B.A.S.F. | 3.5 g |
|   | Aqua purificata | q.s. |
| III | Talcum, Ph. Nord. | 15 g |
|   | Magnesii stearas, Ph. Nord. | 1.5 g |
|   | Weight of 1000 tablets | 325 g |

Weight of 1 tablet: 325 mg
[+] The mesh standard is according to the international system of code DIN 4189/1968.
Punch: 10.5 mm round, flat, scored, bevel-edged Mix the screened substances I thoroughly and then moisten with II, whereupon the mixture is granulated through a stainless sieve No. 10 (mesh 25). Dry the granulate in an oven at a maximum temperature of 40° C. then repeat sieving through sieve No. 10. Add the substances under III and mix thoroughly. Punch tablets with a gross weight of about 325 mg.

EXAMPLE 26

| Suspension for injection 20 mg/ml | |
|---|---|
| Active Compound, mesh 100 | 20 mg |
| Sodium chloride | 8 mg |
| Carboxy methylcellulose | 1 mg |
| Benzyl alcohol | 1 mg |
| Distilled water to make | 1 ml |

EXAMPLE 27

| Oral suspension 5 mg/ml | |
|---|---|
| Active Compound, mesh 100 | 20 mg |
| Sorbitol | 600 mg |
| Flavouring compound | q.s. |
| Colour | q.s. |
| Water to make | 1 ml |

EXAMPLE 28

| Suppositoria a 25 mg | |
|---|---|
| Active Compound | 25 mg |
| Cocoa butter | q.s. |

EXAMPLE 29

| Ointment 2% | |
|---|---|
| Active compound | 2 g |
| Triethanolamine | 1 g |
| Glycerol | 7 g |
| Cetanol | 2.5 g |
| Lanoline | 2.5 g |
| Stearic acid | 20 g |
| Sorbitan monooleate | 0.5 g |
| Sodium hydroxide | 0.2 g |
| Methyl paraben | 0.3 g |
| Propyl paraben | 0.1 g |
| Ethanol | 0.9 g |
| Water to make | 100 g |

EXAMPLE 30

| Capsules a 10 mg | |
|---|---|
| Active compound | 10 mg |
| Magnesium stearate | 2 mg |
| Talcum | 188 mg |

The substances are mixed and filled in capsules.

EXAMPLE 31

| 20 mg sterile powder to be dissolved in water for injection | |
|---|---|
| Watersoluble Active Compound | 10 mg |
| Sodium chloride | 4 mg |
| Methyl paraben | 0.7 mg |
| Propyl paraben | 0.3 mg |

The substances are dissolved in distilled water.
The solution is dispensed in vials and freeze-dried.

EXAMPLE 32

| Injectable solution 20 mg/ml | |
|---|---|
| Watersoluble Active Compound | 20 mg |
| Ascorbic acid | 1 mg |
| Sodium bisulfite | 1 mg |
| Sodium chloride | 6 mg |
| Methyl paraben | 0.7 mg |
| Propyl paraben | 0.3 mg |
| Distilled water to make | 1 ml |

In the foregoing Examples 25–32 relating to compositions the Active Compounds are those covered by the general formula I above or their addition salts with pharmaceutically acceptable inorganic or organic acids. Watersoluble Active Compounds are such addition salts or salts with a pharmaceutically acceptable inorganic or organic cations. Those Active Compounds which are disclosed in the foregoing Examples 1–21 are preferred as Active Compounds as such or in the form of their salts.

Also, it is to be noted that two or more Active Compounds of the invention may be used in combination in the compositions illustrated, and also, if desired, in combination with other pharmacologically active agents.

Various modifications and equivalents will be apparent to one skilled in the art and may be used in the compounds, compositions, and methods of the present invention without departing from the spirit or scope thereof, and it is therefore to be understood that the invention is not to be limited to the specific examples and embodiments disclosed herein.

References

1. Rocklin, R. E., Ann. Repts. Med. Chem. 8 (1973) 284.
2. Eisen, H. N., Immunology, Harper & Row Publishers, Inc., p. 558–70 (1974).
3. Huskisson, E. C. et al, Lancet, 1 (1976) 393.
4. Dieppe, P. A. et al, Agents and Actions 6/5 (1976) 618.
5. Winter, C, A. et al, Proc. Soc. Exp. Biol. Med. 111 (1962) 544.
6. Jones; G. (Ed.), Quinolines, part 1, John Wiley and Sons (1977) p. 93–318.
7. Coppola, G. M. et al, J. Org. Chem. 41 (1976) 825.
8. Coffey, S. (Ed.), Rodd's Chemistry of Carbon Compounds, Elsevier Scientific Publishing Company, Amsterdam, 2nd Ed., vol. III part B (1974) p. 219–44.
9. Dieckmann, W. et al, Ber. 37 (1904) 4627.
10. Hardtmann, G. E. et al, J. Heterocycl. Chem. 12 (1975) 563.
11. Rügheimer, L. et al, Ber. 17 (1884) 736.
12. Newbould, B. B., Brit. J. Pharmacol. 21 (1963) 127.
13. Renoux, G., Pharmac. Ther. A 2 (1978) 397.
14. McOmie, J. F. W., Protective Groups in Organic Chemistry, Plenum Press, London 1977.

What we claim is:

1. A compound having the formula:

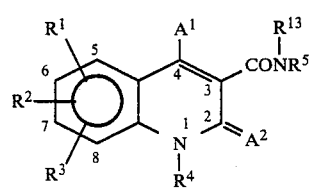

I or a tautomer thereof, wherein the groups $A^1$ and $A^2$ are interchanged and there is a 2,3- rather than a 3,4-double bond; $R^1$, $R^2$ and $R^3$ are independently selected from the group consisting of: hydrogen, lower alkyl, lower alkoxy, halogen, OH, $OCOR^8$, $NR^6R^7$, and $NR^6COR^8$; and where $R^1$ and $R^2$ or $R^2$ and $R^3$ together may also be in the form of a methylenedixoy group; and where only one of $R^1$, $R^2$, and $R^3$ may be $NO_2$;

where $R^4$ is selected from the group consisting of: lower alkyl, lower alkenyl, cycloalkyl, optionally mono- or disubstituted with a substituent selected from the group consisting of lower alkyl, lower alkoxy, OH and $OCOR^8$; and phenyl, optionally mono- or disubstituted with a substituent selected from the group consisting of lower alkyl, lower alkoxy and halogen; and wherein $R^5$ is selected from the group consisting of:

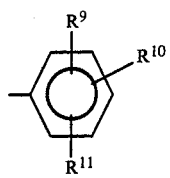

II wherein $R^9$, $R^{10}$, and $R^{11}$ are the same or different and selected from the group consisting of: hydrogen, lower alkyl, lower alkenyl, lower alkoxy, lower alkylthio, halogen, CN, $SO_2CH_3$, OH, $OCOR^8$, $NR^6R^7$, $NR^6COR^8$, $COOR^{12}$, $OCH_2COOR^{12}$, $CH_2COOR^{12}$, $COR^8$, and

wherein m is four or five; and where $R^9$ and $R^{10}$ or $R^{10}$ and $R^{11}$ together also may be in the form of a methylenedioxy group;

wherein $A^1$ is selected from the group consisting of $OR^{12}$, $OCOR^8$, $NR^6R^7$ and $NR^6COR^8$ and $A^2$ is selected from the group consisting of O and $NR^6$; wherein $R^6$ and $R^7$ are selected from the group consisting of hydrogen and lower alkyl; wherein $R^8$ is lower alkyl; wherein $R^{12}$ is selected from the group consisting of lower alkyl and M; and wherein M is selected from the group consisting of hydrogen and pharmaceutically-acceptable inorganic and organic cations; and wherein $R^{13}$ is selected from the group consisting of hydrogen, lower alkyl, optionally substituted with a substituent selected from the group consisting of OH, $OR^8$ and $OCOR^8$, and lower alkenyl; provided that $R^{13}$ is selected from the group consisting of lower alkyl, optionally substituted with a substituent selected from the group consisting of OH, $OR^8$ and $OCOR^8$, and lower alkenyl when $R^5$ is

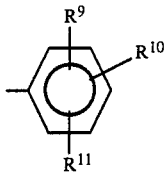

and $R^9$, $R^{10}$, and $R^{11}$ are selected from the group consisting of lower alkyl, lower alkenyl and lower alkoxy; and addition salts with pharmaceutically-acceptable inorganic or organic acids; the term "lower" when used herein meaning in each case that the group referred to may be straight or branched and contains one to four carbon atoms, inclusive.

2. A compound according to claim 1 characterized in that $R^{13}$ is selected from the group consisting of lower alkyl optionally substituted or lower alkenyl, $A^1$ is OH and $A^2$ is O, and the $R^4$ is lower alkyl.

3. A compound according to claim 1 characterized in that $A^1$ is selected from the group consisting of $NR^6R^7$ and $NR^6COR^8$, $A^2$ is O, $R^4$ is lower alkyl and where $R^6$, $R^7$ and $R^8$ have the meanings as defined above.

4. A compound according to claim 1 characterized in that $R^{13}$ is hydrogen $R^5$ is the group II as defined above wherein $R^9$, $R^{10}$ and $R^{11}$ are selected from the group consisting of halogen, OH, $OCOR^8$, $NR^6R^7$, $NR^6COR^8$,

$COOR^{12}$, $OCH_2COOR^{12}$ and $CH_2COOR^{12}$, where $R^6$, $R^7$, $R^8$, $R^{12}$ and m have the meanings as defined above.

5. A compound according to claim 1 characterized in that at least two of the substituents $R^1$, $R^2$ and $R^3$ are hydrogen and at least one of the substituents $R^9$, $R^{10}$ and $R^{11}$ is hydrogen.

6. A compound according to claim 1 selected from the group consisting of:
(a) N-(4-dimethylaminophenyl)-1,2-dihydro-4-hydroxy-1-methyl-2-oxo-quinoline-3-carboxamide
(b) N-(4-carboxymethylphenyl)-1,2-dihydro-4-hydroxy-1-methyl-2-oxo-quinoline-3-carboxamide
(c) N-(4-hydroxyphenyl)-1,2-dihydro-4-hydroxy-1-methyl-2-oxo-quinoline-3-carboxamide
(d) N-phenyl-N-methyl-1,2-dihydro-4-hydroxy-1-methyl-2-oxo-quinoline-3-carboxamide
(e) N-methyl-N-phenyl-4-amino-1,2-dihydro-1-methyl-2-oxo-quinoline-3-carboxamide
(f) N-phenyl-1,2-dihydro-4-hydroxy-2-imino-1-methyl-quinoline-3-carboxamide
(g) N-methyl-N-phenyl-1,2-dihydro-6-dimethylamino-4-hydroxy-1-methyl-2-oxo-quinoline-3-carboxamide
(h) N-(4-methoxyphenyl)-N-methyl-1,2-dihydro-4-hydroxy-1-methyl-2-oxo-quinoline-3-carboxamide
(i) N-(4-chlorophenyl)-N-methyl-1,2-dihydro-4-hydroxy-1-methyl-2-oxo-quinoline-3-carboxamide
(j) N-(2-hydroxyphenyl)-N-methyl-1,2-dihydro-4-hydroxy-1-methyl-2-oxo-quinoline-3-carboxamide,
and said compounds (a)–(j) in the form of salts with pharmaceutically-acceptable inorganic or organic cations or addition salts with pharmaceutically-acceptable inorganic or organic acids.

7. A composition of matter suitable for enhancing immunity comprising as an active ingredient an effective immunizing amount of one or more of the compounds having the formula I as defined in claim 1 together with a pharmaceutically-acceptable carrier.

8. The composition of claim 7 wherein the active ingredient is a compound according to claim 6 present in an amount between about 0.05 and 15 percent by weight of the composition.

9. A compound according to claim 1 wherein $R^9$, $R^{10}$ and $R^{11}$ are the same or different and are selected from the group consisting of hydrogen, lower alkyl, lower alkenyl, lower alkoxy lower alkylthio, CN, $SO_2CH_3$, OH, $OCOR^8$, $NR^6R^7$, $NR^6COR^8$, $COOR^{12}$, $OCH_2COOR^{12}$, $CH_2COOR^{12}$, $COR^8$ and

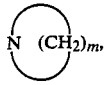

wherein m is four or five and where $R^9$ and $R^{10}$ and $R^{10}$ and $R^{11}$ together also may be in the form of a methylenedioxy group.

10. A compound according to claim 1 selected from the group consisting of
 (a) N-(4-dimethylaminophenyl)-1,2-dihydro-4-hydroxy-1-methyl-2-oxo-quinoline-3-carboxamide,
 (b) N-(4-carboxymethylphenyl)-1,2-dihydro-4-hydroxy-1-methyl-2-oxo-quinoline-3-carboxamide,
 (c) N-(4-hydroxyphenyl)-1,2-dihydro-4-hydroxy-1-methyl-2-oxo-quinoline-3-carboxamide,
 (d) N-phenyl-N-methyl-1,2-dihydro-4-hydroxy-1-methyl-2-oxo-quinoline-3-carboxamide,
 (e) N-methyl-N-phenyl-4-amino-1,2-dihydro-1-methyl-2-oxo-quinoline-3-carboxamide,
 (f) N-phenyl-1,2-dihydro-4-hydroxy-2-imino-1-methyl-quinoline-3-carboxamide,
 (g) N-methyl-N-phenyl-1,2-dihydro-6-dimethylamino-4-hydroxy-1-methyl-2-oxo-quinoline-3-carboxamide,
 (h) N-(4-methoxyphenyl)-N-methyl-1,2-dihydro-4-hydroxy-1-methyl-2-oxo-quinoline-3-carboxamide,
 (i) N-(2-hydroxyphenyl)-N-methyl-1,2-dihydro-4-hydroxy-1-methyl-2-oxo-quinoline-3-carboxamide,
and said compounds (a)–(i) in the form of salts with pharmaceutically-acceptable inorganic or organic cations or addition salts with pharmaceutically-acceptable inorganic or organic acids.

11. N-phenyl-N-methyl-1,2-dihydro-4-hydroxy-1-methyl-2-oxo-quinoline-3-carboxamide.

* * * * *

UNITED STATES PATENT AND TRADEMARK OFFICE
CERTIFICATE OF CORRECTION

PATENT NO. : 4,738,971

DATED : April 19, 1988

INVENTOR(S) : ERIKSOO et al

It is certified that error appears in the above-identified patent and that said Letters Patent is hereby corrected as shown below:

Title page:

[73] Assignee: Aktiebolaget Leo, Helsingborg, Sweden

[75] Inventors: Edgar Eriksoo, Helsingborg; Eva B. M. Sandberg, Löddeköpinge; Lars J. T. Stålhandske, Helsingborg, all of Sweden Signed and Sealed this Sixteenth Day of August, 1988

Attest:

DONALD J. QUIGG

Attesting Officer

Commissioner of Patents and Trademarks